US012685574B2

(12) United States Patent
Korman et al.

(10) Patent No.: US 12,685,574 B2
(45) Date of Patent: Jul. 21, 2026

(54) SYSTEM AND METHOD FOR WEIGHT BEARING SIMULATION DURING FOOT SURGERY

(71) Applicant: WRIGHT MEDICAL TECHNOLOGY, INC., Memphis, TN (US)

(72) Inventors: Zachary Korman, St. Louis, MO (US); Salman Chegini, Uetikon am See (CH); Jesse G. Moore, Germantown, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 27 days.

(21) Appl. No.: 18/796,430

(22) Filed: Aug. 7, 2024

(65) Prior Publication Data

US 2025/0057573 A1 Feb. 20, 2025

Related U.S. Application Data

(60) Provisional application No. 63/579,611, filed on Aug. 30, 2023, provisional application No. 63/520,411, filed on Aug. 18, 2023.

(51) Int. Cl.
| | |
|---|---|
| *A61B 17/88* | (2006.01) |
| *A61B 17/00* | (2006.01) |
| *A61B 17/56* | (2006.01) |
| *A61B 90/00* | (2016.01) |

(52) U.S. Cl.
CPC ........ *A61B 17/885* (2013.01); *A61B 17/8861* (2013.01); *A61B 17/8869* (2013.01); *A61B 2017/00477* (2013.01); *A61B 2017/564*

(2013.01); *A61B 2017/567* (2013.01); *A61B 90/08* (2016.02); *A61B 2090/0807* (2016.02)

(58) Field of Classification Search
CPC ... A61B 5/1036; A61B 5/1074; A61B 17/885; A61B 17/8861; A61B 17/8869; A61B 90/08; A61B 2090/0807; A61B 2017/00477; A61B 2017/564; A61B 2017/567
USPC .................................. 606/86 R, 96–98, 104
See application file for complete search history.

(56) References Cited

U.S. PATENT DOCUMENTS

| | | | | |
|---|---|---|---|---|
| 1,383,928 A | * | 7/1921 | Gassette | ............... A61F 5/0111 482/79 |
| 2,067,567 A | | 1/1937 | Adam | |
| 9,750,516 B2 | * | 9/2017 | Tochigi | ................. A61B 17/15 |
| 10,292,887 B2 | * | 5/2019 | Kang | ................. A61G 13/1245 |

(Continued)

FOREIGN PATENT DOCUMENTS

| | | |
|---|---|---|
| CN | 111887932 A | 11/2020 |
| WO | 2021206835 A1 | 10/2021 |

OTHER PUBLICATIONS

Z&Z Medical, Inc., "Weight Bearing Cassette/DR. Panel Holder", https://www.zzmedical.com/exclusives/weight-bearing-cassette-dr-panel-holder.html, accessed from internet on Mar. 6, 2023.

(Continued)

*Primary Examiner* — Jessica Weiss
(74) *Attorney, Agent, or Firm* — DUANE MORRIS LLP

(57) ABSTRACT

A system to provide weight bearing simulation includes a plate; a strap to hold the plate to a foot; and a device configured to mount to the plate and adjust a position of the foot to the plate.

19 Claims, 21 Drawing Sheets

(56) References Cited

U.S. PATENT DOCUMENTS

| | | | |
|---|---|---|---|
| 11,751,892 B2* | 9/2023 | Woodard | A61B 17/025 |
| | | | 606/87 |
| 11,766,270 B2* | 9/2023 | McGinley | A61B 17/88 |
| | | | 606/86 R |
| 11,779,359 B2* | 10/2023 | Sayger | A61B 17/15 |
| | | | 606/87 |
| 11,850,170 B2* | 12/2023 | Coulange | A61B 17/1775 |
| 11,864,778 B2* | 1/2024 | McGinley | A61F 2/4202 |
| 2008/0132897 A1* | 6/2008 | Livorsi | A61B 90/36 |
| | | | 606/88 |
| 2011/0253151 A1* | 10/2011 | Tochigi | A61B 17/15 |
| | | | 128/845 |
| 2013/0090662 A1* | 4/2013 | Hanson | A61B 90/00 |
| | | | 606/86 R |
| 2016/0331392 A1 | 11/2016 | Mire et al. | |
| 2018/0110530 A1* | 4/2018 | Wagner | A61B 17/151 |
| 2019/0029700 A1* | 1/2019 | Free | A61B 17/1682 |
| 2021/0038235 A1 | 2/2021 | Free et al. | |

OTHER PUBLICATIONS

Extended European Search Report issued in connection with corresponding European Patent Application No. 24193896.8, Jan. 17, 2025, 9 pages.

\* cited by examiner

FIG. 19A                    FIG. 19B

SYSTEM AND METHOD FOR WEIGHT BEARING SIMULATION DURING FOOT SURGERY

CROSS REFERENCE TO RELATED APPLICATIONS

This application claims the benefit of U.S. Provisional Patent Application No. 63/520,411, filed Aug. 18, 2023, and 63/579,611, filed Aug. 30, 2023 the entire contents of each of which is incorporated by reference for all purposes as if fully set forth herein.

FIELD OF DISCLOSURE

The present disclosure relates to a surgical system that simulates a weight bearing plane and holds a guiding instrument to place implants in a foot.

BACKGROUND

In many surgical procedures, it is helpful to reference the weight-bearing plane. In some cases, it is also useful to reference instrumentation and implant placement with respect to the weight-bearing plane. Due to the need to maintain a sterile field, a weight-bearing simulator is often used. Typically, this takes form as an aluminum lid to a tray that happens to be present in the operating room. In some surgeries of the foot or metatarsal phalangeal (MTP) joints, using this lid allows the surgeon or assistant to push against the foot to simulate weight bearing. However, current techniques require multiple worker hands to hold the lid in place while inserting guide wires or k-wires through an unrestrained guide into the restrained foot position. Additionally, this conventional method provides no additional features to help orient any medical devices or align bones to this simulated weight-bearing plane. Therefore, a system or an instrument including a way to simulate a weight-bearing plane and hold a surgical guiding instrument to place implants is desired.

SUMMARY

To overcome the problems described above, embodiments of the present disclosure include a weight bearing simulator including a universal clamp that connects to flat trays, lids or plates. The universal clamp is adjustable and includes feature for mounting a surgical guide in an anatomically restrained foot position, which simulates weight bearing of a foot when it is desired for correct surgical alignment. This clamp also works with surgical guides. Another embodiment of the present disclosure includes a unique plate used in place of a generic tray as a weight-bearing plane. Another embodiment of the present disclosure includes an angled support to set a foot in position with the weight-bearing plane.

Embodiments disclosed provide the following features and advantages: (i) a flat surface to simulate weight bearing as needed, (ii) static and adjustable mechanisms to conform to different sized feet while maintaining the medial border in the appropriate position to use the operative aid features, (iii) hallux valgus adjustment and lateral phalanx support to correct hallux valgus during a procedure, (iv) pegboard holes to adjust position of procedural aid features based on foot size, (v) shims to vertical orient the phalanx during a procedure, (vi) support to hold a foot above a surface and more anatomically depending on patient positioning.

According to an embodiment, a system to provide weight bearing simulation includes a plate; a strap to hold the plate to a foot; and a device configured to mount to the plate and adjust a position of the foot to the plate.

In an aspect, the plate includes a slot configured for the strap to be fed through.

In an aspect, the plate includes a plurality of holes to mount the device.

In an aspect, a first side of the plate is configured to be secured to a right foot and a second side of the plate is configured to be secured to a left foot.

In an aspect, the device includes a heel block configured to orient a heel of the foot to the plate.

In an aspect, the heel block is adjustable to accommodate various size feet.

In an aspect, the device includes a pusher configured to adjust a position of a bone of the foot.

In an aspect, the device includes a distractor configured to apply force to separate bones of the foot.

The system can further include a support configured to secure the plate to the support.

In another embodiment, a system to provide weight bearing simulation includes a clamp to secure a plate; an adjuster to provide adjustment of a foot in contact with the plate.

In an aspect, the clamp includes a base, an arm, and a lead screw.

In an aspect, the adjuster includes a lead screw and dowel mechanism.

In an aspect, the adjuster includes a body, a lead screw, and a guide interface.

In an aspect, the guide interface is configured to mount a surgical guide.

In another embodiment, a method of performing foot surgery includes providing a plate; and securing a foot to the plate.

In an aspect, securing the foot to the plate includes locking a heel of the foot into place on the plate.

In an aspect, securing the foot to the plate includes mounting a stabilizer to the plate and inserting a k wire through the stabilizer and into the foot.

The method can further include simulating weight bearing by applying a force to the foot via the plate.

The method can further include attaching a guide to the plate; and adjusting alignment of a first bone and a second bone using the guide.

The method can further include distracting the first bone and the second bone using the guide.

The above and other features, elements, characteristics, steps, and advantages of the present invention will become more apparent from the following detailed description of preferred embodiments of the present invention with reference to the attached drawings.

BRIEF DESCRIPTION OF THE DRAWINGS

The inventive concepts of the present disclosure will be described in more detail in conjunction with the following drawing figures. The structures in the drawing figures are illustrated schematically and are not intended to show actual dimensions.

FIG. 8A to FIG. 13 are used to describe another embodiment of the present disclosure of a foot plate with deformity correction features.

DETAILED DESCRIPTION

Figure 1:
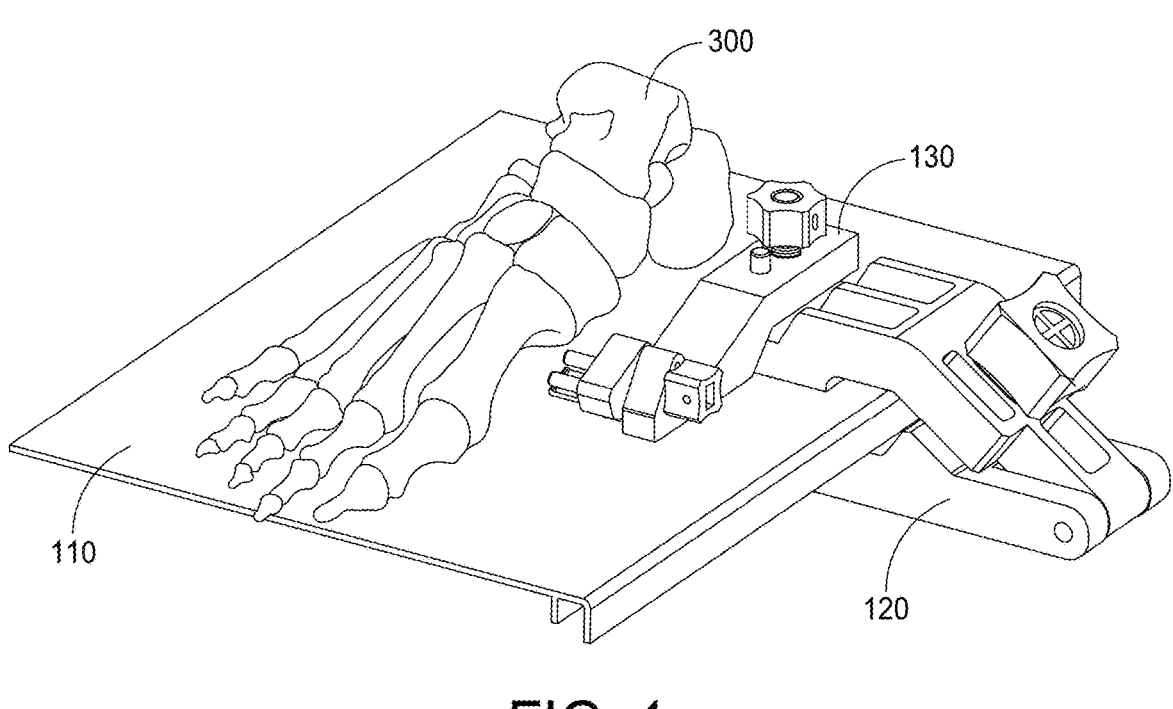
FIG. 1 to FIG. 4 are different views of a system to provide weight bearing simulation according to a first embodiment.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Unless otherwise expressly stated, it is in no way intended that any method set forth herein be construed as requiring that its steps be performed in a specific order, nor that with any apparatus, specific orientations be required, unless specified as such. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

Figure 2:
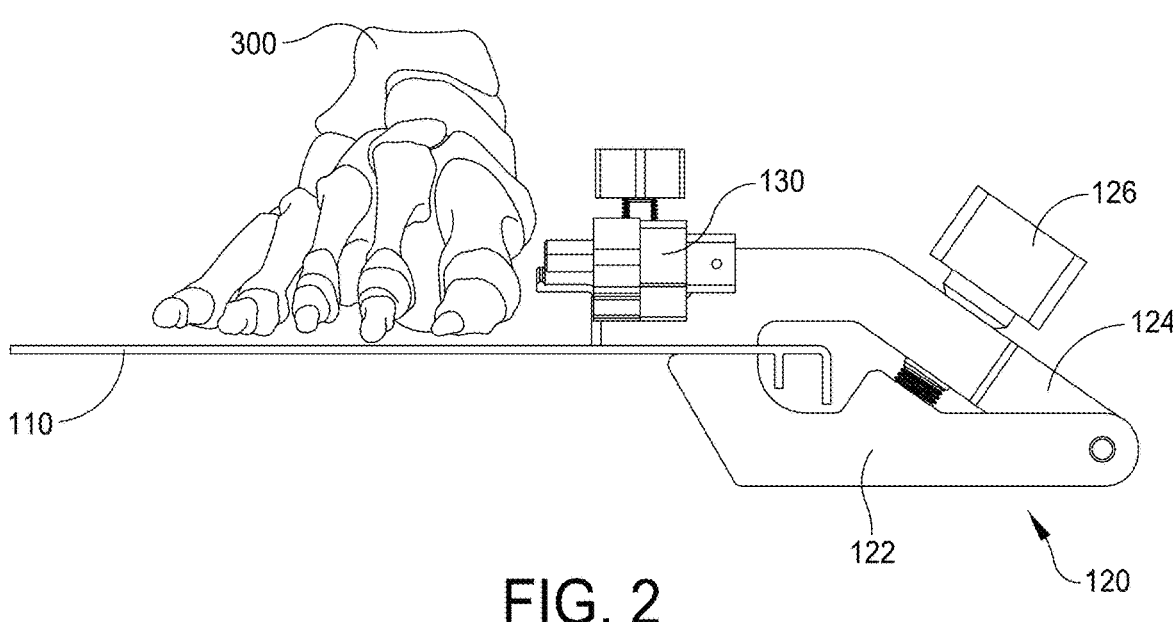
Figure 3:
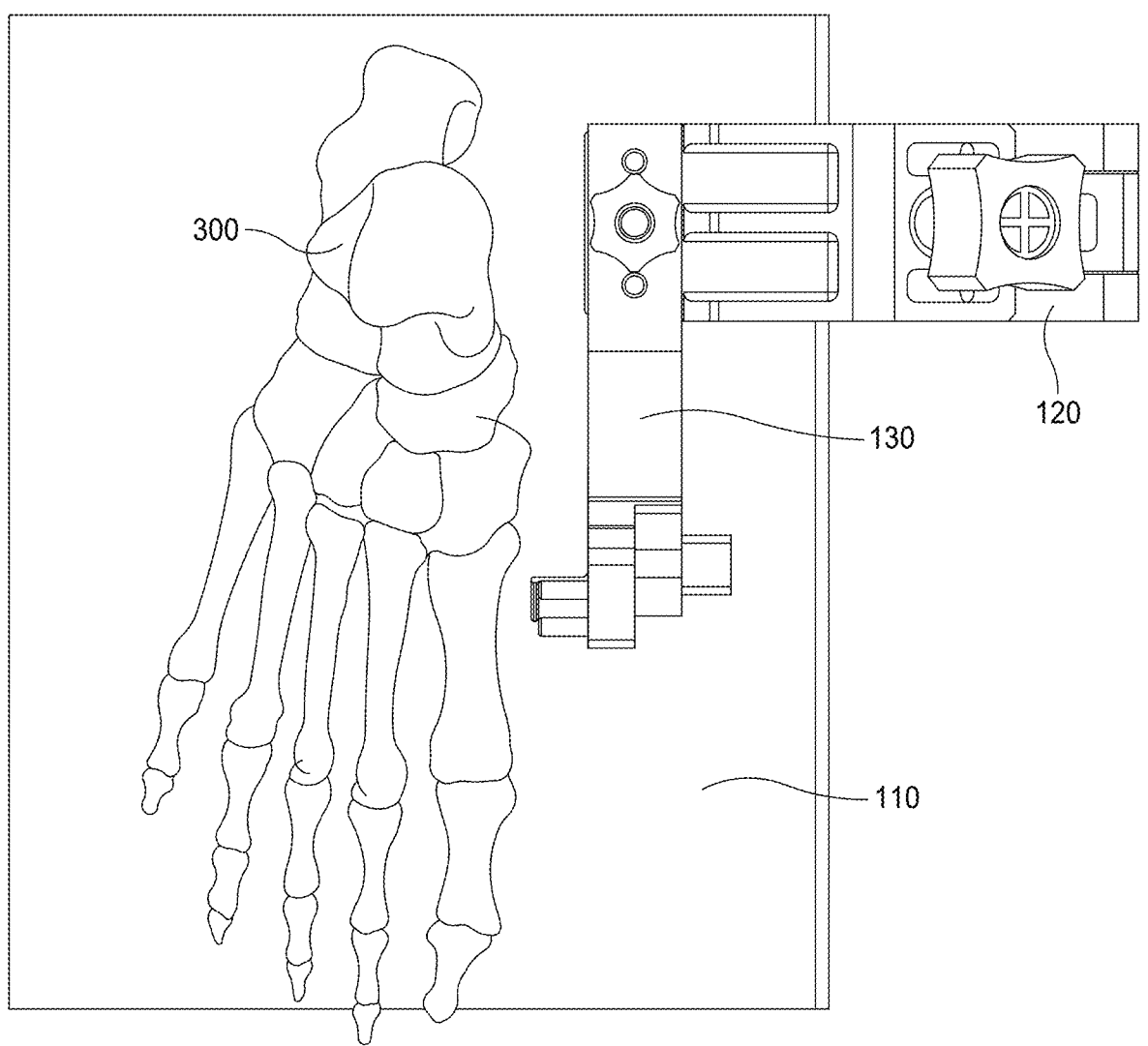
Figure 4:
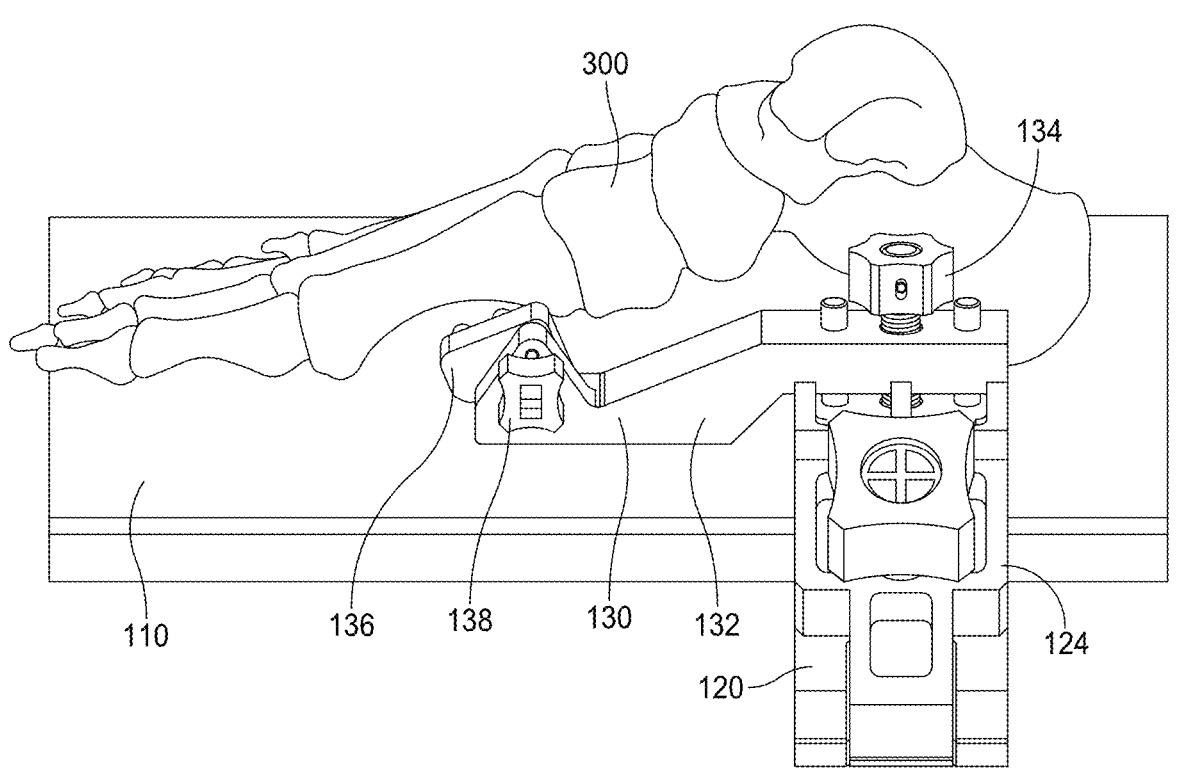

FIGS. 1-4 are different views of a clamp system 100 to provide weight-bearing simulation used in an osteotomy procedure on a foot, according to an embodiment of the present disclosure. The disclosed clamp system 100 includes a clamp to add features to trays and lids in the operating room that surgeons already use. The clamp utilizes a hinge and screw mechanism to create substantial clamping force to hold an osteotomy or fusion guide firmly onto the tray lid or plate. As shown, the clamp system 100 can include a plate 110 and a clamp 120 that secures the plate 110 in relation to an adjuster 130. FIG. 1 is a perspective view, FIG. 2 is a side view, FIG. 3 is a top view, and FIG. 4 is a front view of the clamp system 100 including the plate 110, the clamp 120, and the adjuster 130, in relation to bones of a right foot 300. The plate 110 can be a tray, a lid, or any other suitable structure that is substantially planar, configured to be secured by the clamp 120, and strong enough to provide suitable weight bearing pressure on a foot.

FIG. 2 shows that the clamp 120 can include a base 122, an arm 124, and a knob 126 to a screw. The clamp 120 can be configured such that both of the base 122 and the arm 124 include flat surfaces oriented to oppose each other in which to secure the plate 110 in between. Force to secure the plate 110 between the base 122 and the arm 124 can be provided by a knob 126 to turn a screw fed through the arm 124 to the base 122 to draw the base 122 and the arm 124 together to secure the plate 110 in between. Optionally, a screw mechanism or a lever and cam mechanism can be used rather than then knob 126. A side view of an exemplary cam mechanism 1600 is provided in FIG. 16.

The adjuster 130 can be attached to the arm 124 of the clamp 120. Referring to FIG. 4, the adjuster 130 can include a body 132, a first knob 134 for rotating a perpendicular lead screw 133, a guide interface 136, and a second knob 138. The lead screw 133 and associated dowel mechanism provides linear adjustment in a direction perpendicular to the weight-bearing plane that is parallel to the major surfaces of the plate 110. Force to move the adjuster 130 relative to the arm 124 can be provided by the first knob 134 to turn a lead screw fed through the body 132 to the arm 124. Similarly, force to loosen or tighten the guide interface 136 relative to the body 132 can be provided by the second knob 138 to turn a screw fed through the body 132 to the guide interface 136.

Figure 5:
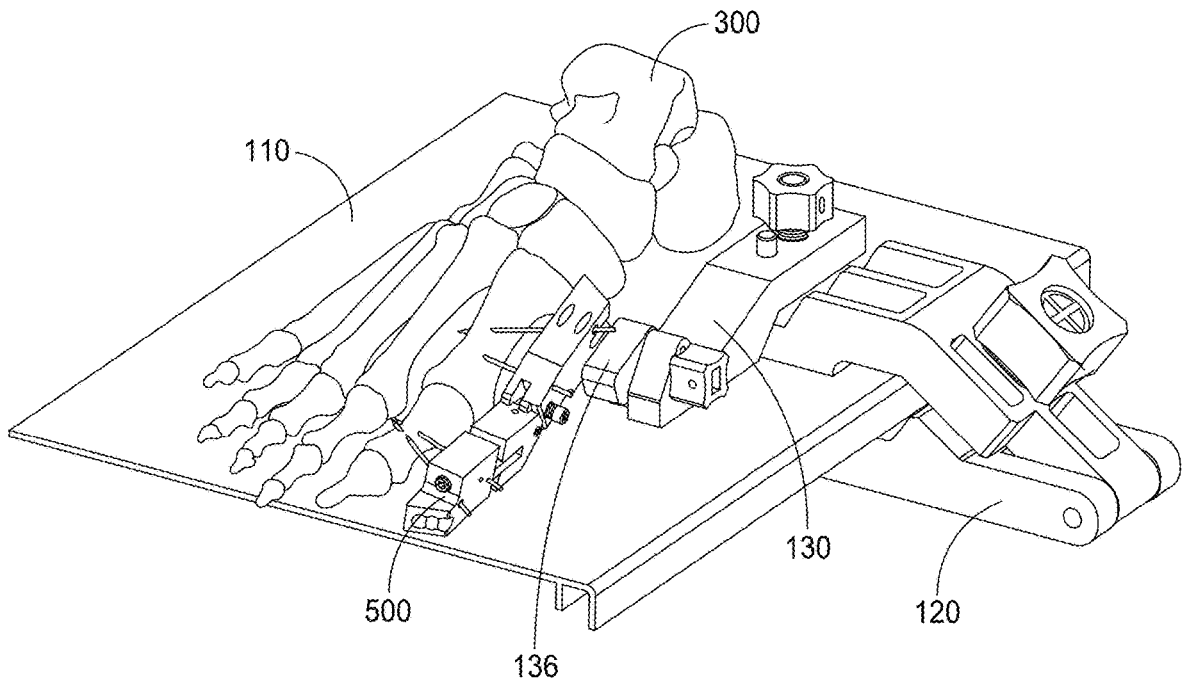
FIG. 5 shows a surgical guide attached to a clamp system.

FIG. 5 shows a surgical guide 500 attached to the clamp system 100 via the guide interface 136. The surgical guide 500 can be used to assist a surgeon during surgery for setting the trajectory of k-wires and fixation screws. For example, during a metatarsophalangeal (MTP) joint fusion surgical procedure, the first phalanx bone is separated from the metatarsal bone. The metatarsal and phalanx are realigned and then fixed in relation with two screws. K-wires are traditionally used to hold the phalanx bone and the metatarsal head at the intended translated position during the subsequent screw fixation procedure. The clamp system 100 can be used to simulate weight-bearing and adjust the surgical guide 500 relative to a patient's foot. The surgical guide 500 can be used to arrange and lock desired angles for dorsiflexion and varus/valgus in the foot bones.

Figure 6:
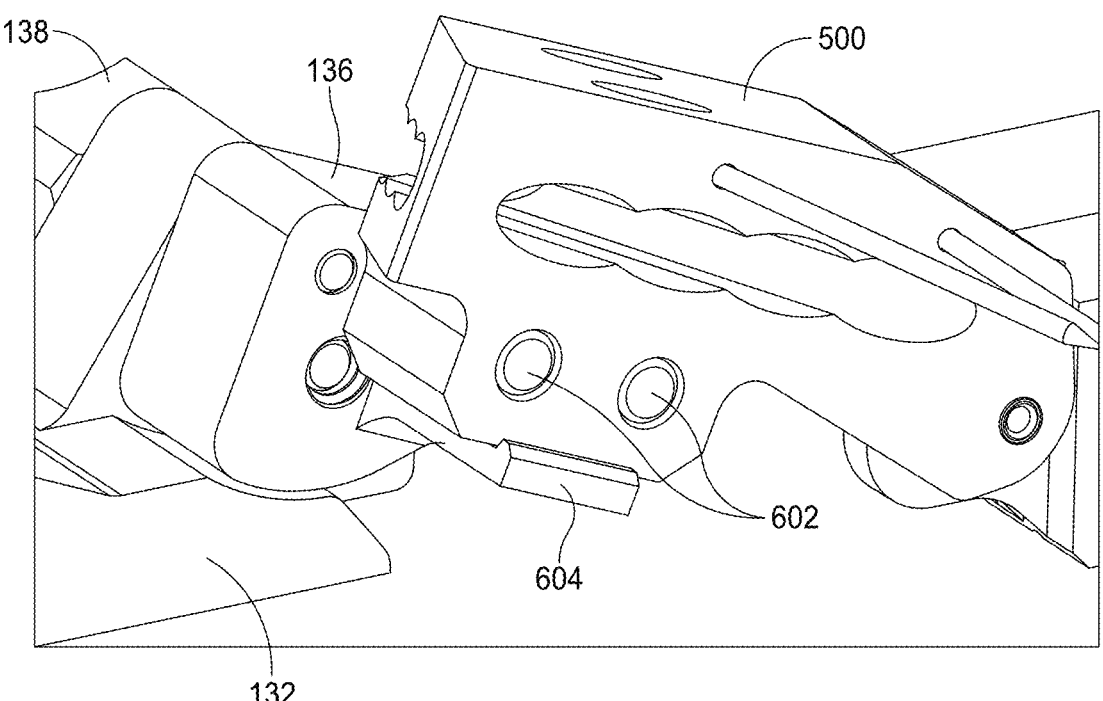
FIG. 6 shows an example of how such a surgical guide can be attached to a guide interface.

FIG. 6 shows an example of how such a surgical guide 500 can be attached to the guide interface 136. The guide interface 136 can include posts 602 that protrude from one side of the guide interface 136 that fit into corresponding holes of the surgical guide 500 to orient the surgical guide 500. The guide interface 136 can also include a locking tab 604 used to retain the surgical guide 500 in place on the posts 602. However, any suitable connection mechanism can be used. Alternatively, the surgical guide 500 can be integrally defined with a clamp system if it suites details of the surgical procedure.

Figure 7:
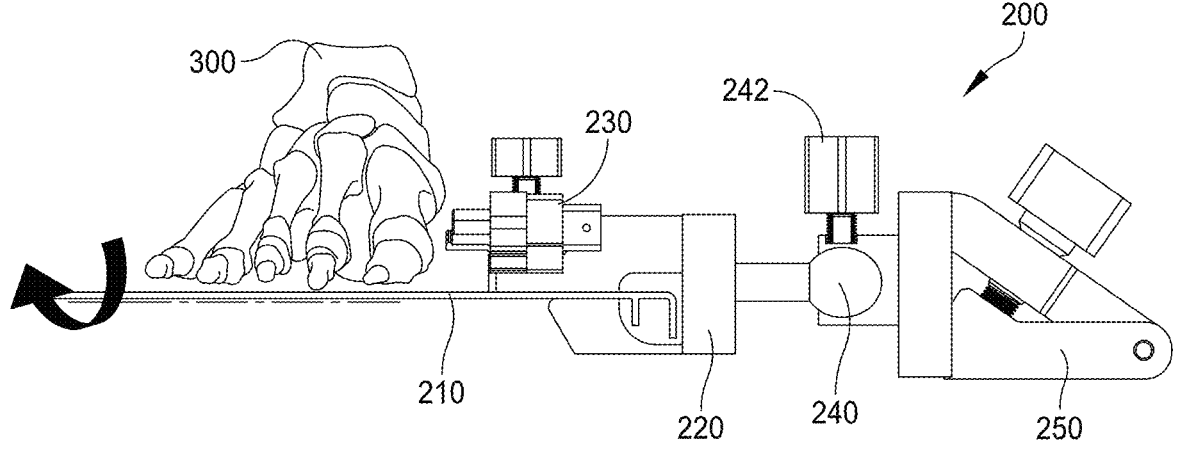
FIG. 7 is a side view of a clamp system according to another embodiment of the present disclosure.

FIG. 7 is a side view of a clamp system 200 according to another embodiment of the present disclosure. As shown, the clamp system 200 can include a plate 210 that can be used as a weight-bearing plane for a foot 300 during surgery and a clamp 220 to secure the plate 210 similar to the clamp 120 previously described. The clamp system 200 can also include a pivot joint 240 to allow for flexion or extension of the foot 300 in a desired angle if the surgeon decides that is beneficial before applying a weight bearing force. The pivot joint 240 can be configured as a hinge to rotate the clamp 210 with the plate 210 in two directions. Alternatively, the pivot joint 240 can be configured as a ball and socket so that the clamp 210 with the plate 210 can be rotated in multiple directions. The pivot joint 240 can include a knob 242 with a lead screw to lock and unlock the pivot joint 240 by tightening or loosening the knob 242 and lead screw against rotational features of the pivot joint 240. The table clamp 250 can be pivotably attached to the clamp system 200, and is used to fixate the clamp 220 onto the surgical table using a screw under the surgical table, or another suitable mechanism. The clamp system 200 can be elevated relative to the surgical table so that the angulation of the plate 210 is possible in several directions.

Figures 8A, 8B:
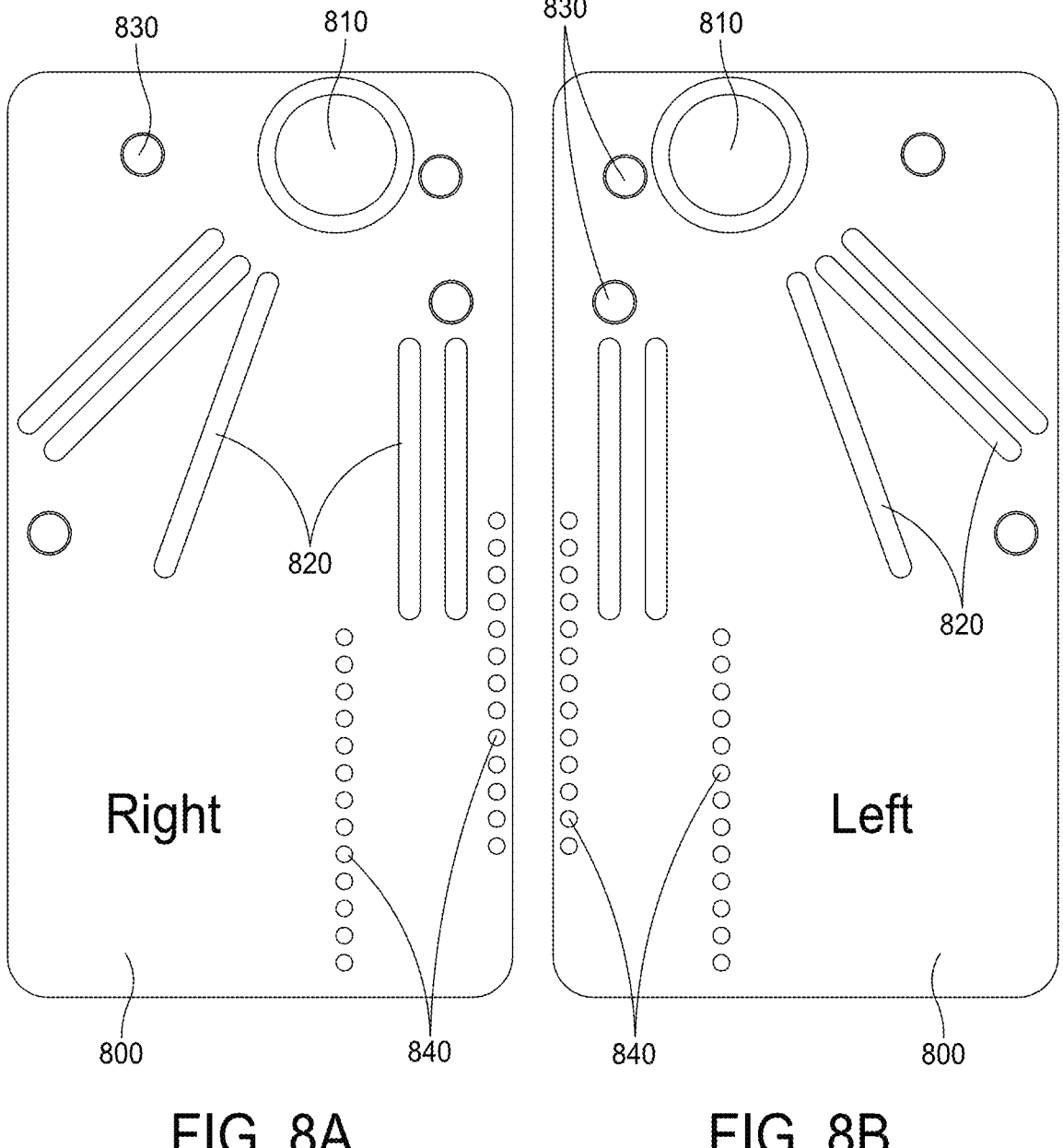

FIGS. 8A-13 are used to describe another embodiment of the present disclosure. This system provides features to fixate feet of variable lengths to one flat, sturdy, radiolucent plate 800 for simulated weight bearing. FIG. 8A depicts one side of the plate 800 used for a right foot and FIG. 8B depicts the opposite side of the plate 800 used for a left foot. The plate 800 can be substantially planar. Although shown as having a rectangular shape, the plate 800 can be defined to have any suitable shape. The features provided on the plate 800 can include a heel locator 810, a plurality of slots 820, a plurality of fixture holes 830, and a plurality of peg board holes 840.

The heel locator 810 can be a recess, depression, hole, or marked indicator in the plate 800 in which a patient's heel can be located. The plurality of slots 820 can be used to route an adjustable strap through the plate 800 and across a mid-foot to secure the plate 800 to the patient's foot, as described with respect to FIG. 9. The plurality of fixture holes 830 can be used to mount blocks or fixtures to orient and secure the patient's foot, as described with respect to FIGS. 10 and 11. The plurality of pegboard holes 840 can be used to mount blocks or adjustment fixtures to orient and secure bones of the patient's foot, as described with respect to FIGS. 12 and 13. Optionally, at least some of the pegboard holes 840 can be replaced with a slot, as discussed below with respect to FIG. 17.

Figure 9:
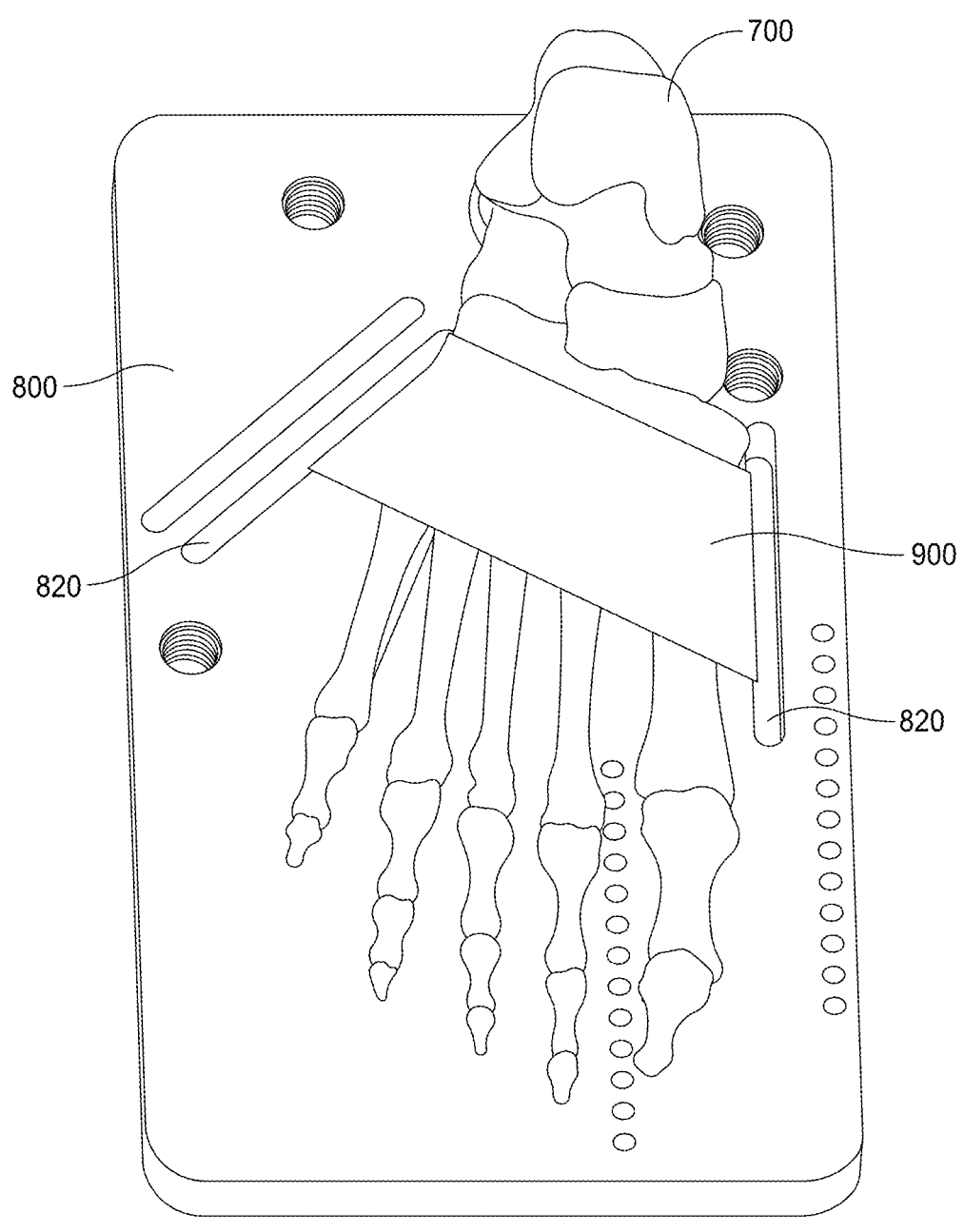

FIG. 9 shows the plate 800 secured to a patient's right foot 700. The plate 800 has been oriented such that the heel of the foot 700 is located in the heel locator 810 (not visible). An adjustable strap 900 has been fed through two of the slots 820 and over the foot 700 and secured by a fastening mechanism such as hook and loop, a snap, a button, a buckle, or any other suitable means. Slots 820 in which to feed the strap 900 can be selected based on the size of the foot 700.

Figure 10:
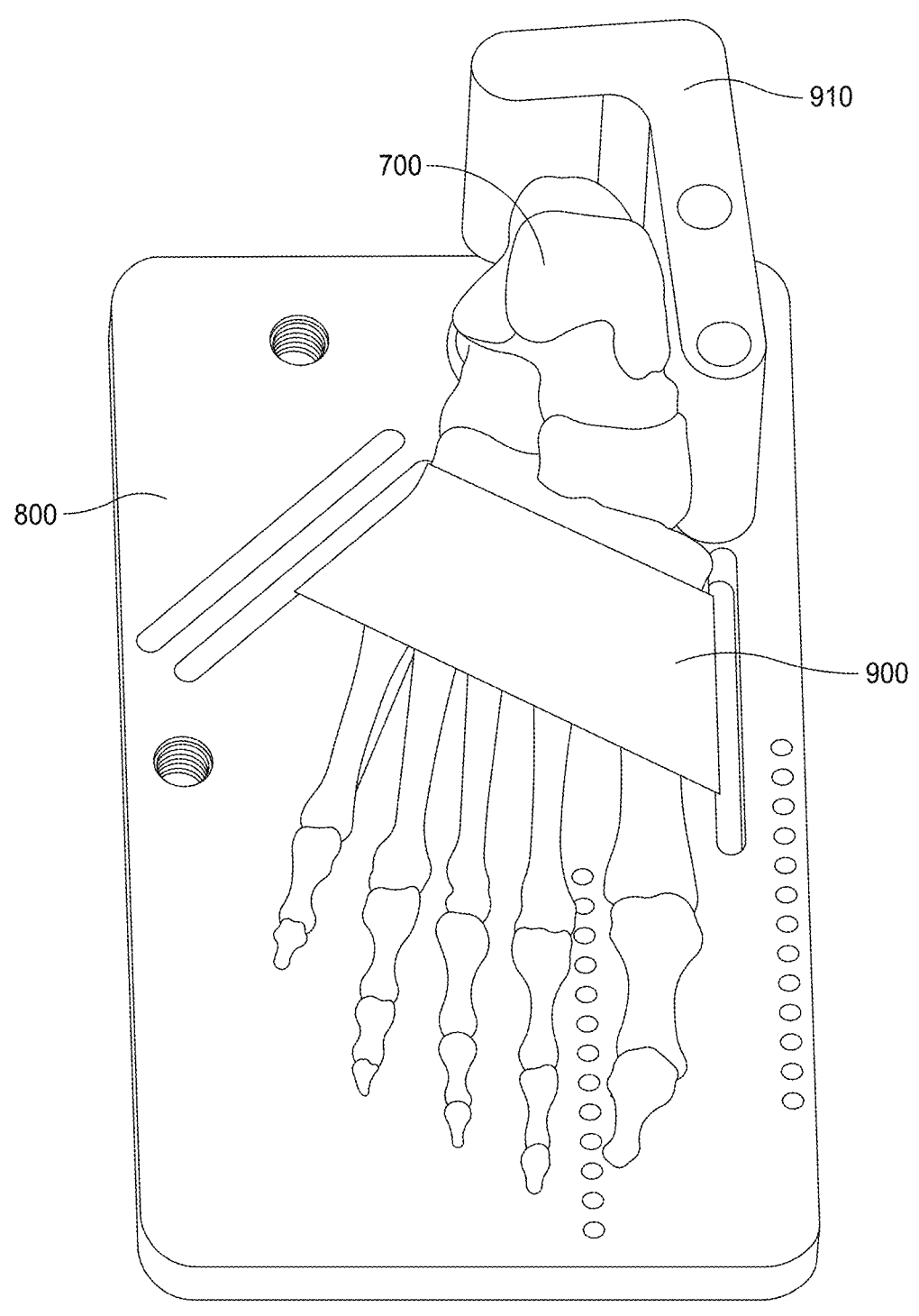

FIG. 10 shows that a posterior-medial heel block 910 can be placed using dowels with spring plungers, for example, into fixture holes 830, shown in FIG. 8. Optionally, another suitable mechanism, like a threaded connection, can also be used to fasten the heel block 910 to the plate 800. The posterior-medial heel block 910 can be substantially 'L' shaped with perpendicular sides such that the heel of the patient's foot 700 can fit into and be supported by the angle created by the two sides.

Figure 11:
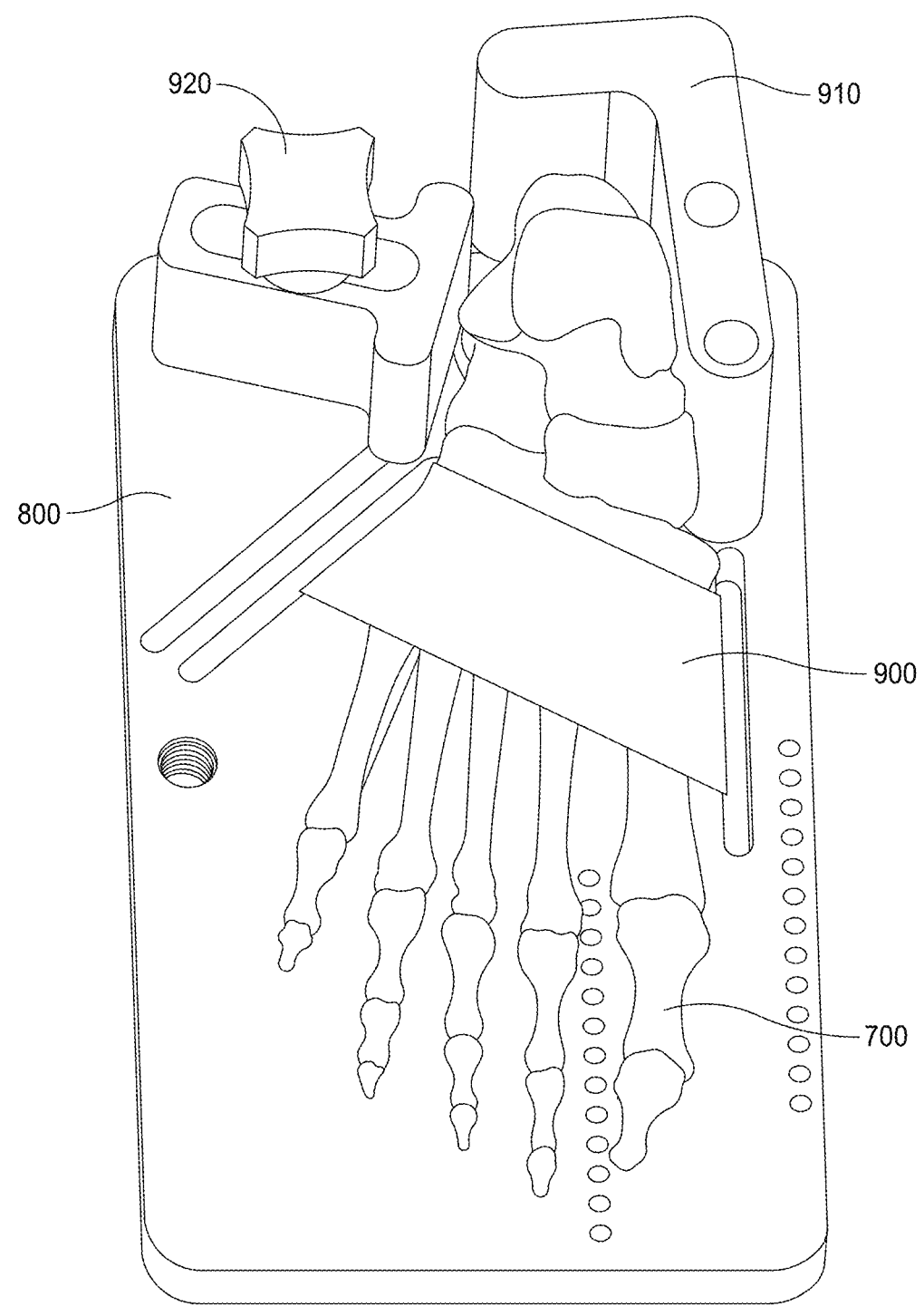

FIG. 11 shows that an adjustable lateral heel block 920 can be placed into a fixture hole 830 (not visible) on the other side of the foot 700 from the posterior-medial heel block 910. The lateral heel block 920 can be connected to plate 800 directly with a threaded connection. A knob 922 can be threaded into the hole 830 of the plate 800 to secure the lateral heel block 920. When loose, the lateral heel block 920 can rotate or translate, but be locked into place when the knob 922 is tightened.

The lateral heel block 920 can include an adjustment mechanism such as including a body with a slot and a knob to a screw through the slot to accommodate different size feet. The screw can be loosened so that the body of the lateral heel block 920 can be moved to a position to secure the foot 700 between the posterior-medial heel block 910 and the lateral heel block 920. Once the lateral heel block 920 is in position, the screw via the knob 922 can be tightened to lock the lateral heel block 920 in place.

Figure 12:
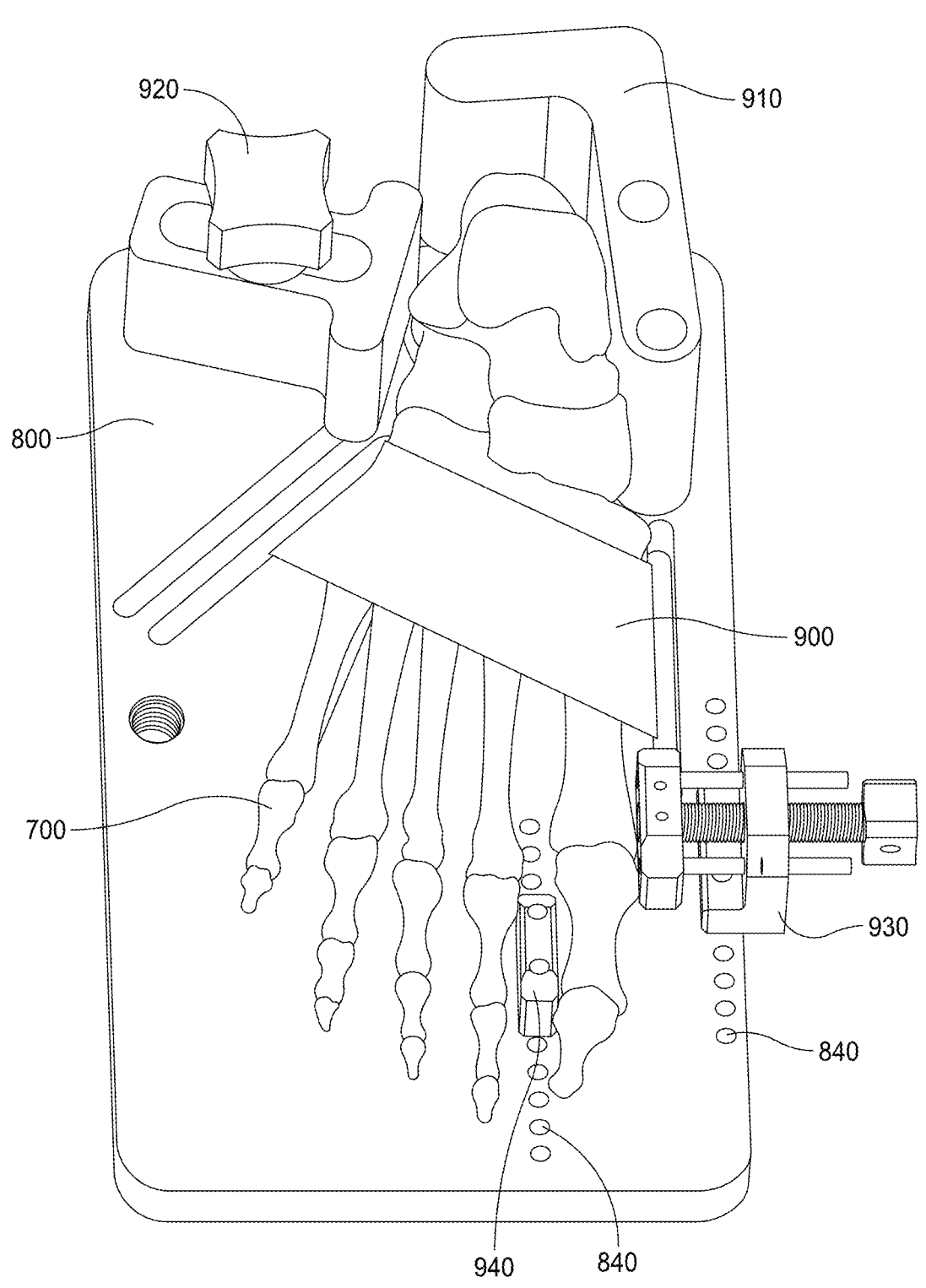
Figure 17:
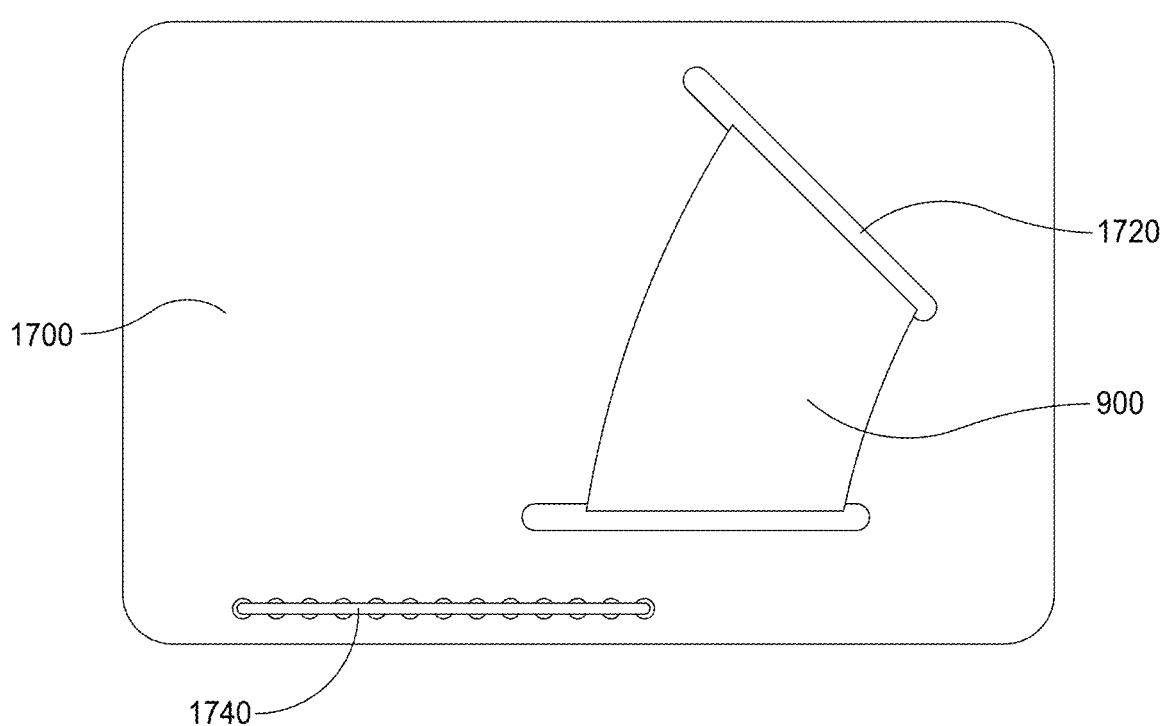
FIG. 17 is a top view of a foot plate.

FIG. 12 shows that a hallux-valgus pusher 930 and a lateral phalanx support 940 can be placed using dowels with spring plungers into pegboard holes 840. Optionally, a slot or slots can be used in place of the pegboard holes 840 to allow placement and distal-proximal adjustment of the pusher 930 and the support 940. For example, FIG. 17 shows an embodiment of a plate 1700 that includes a strap 900 across slots 1720 and including a slot 1740 rather than pegboard holes. The surface of the slot 1740 can include recesses, scalloped-shaped recesses, knurling, or ridges to increase the connection strength between the pusher 930 and the plate 1700.

Figure 13:
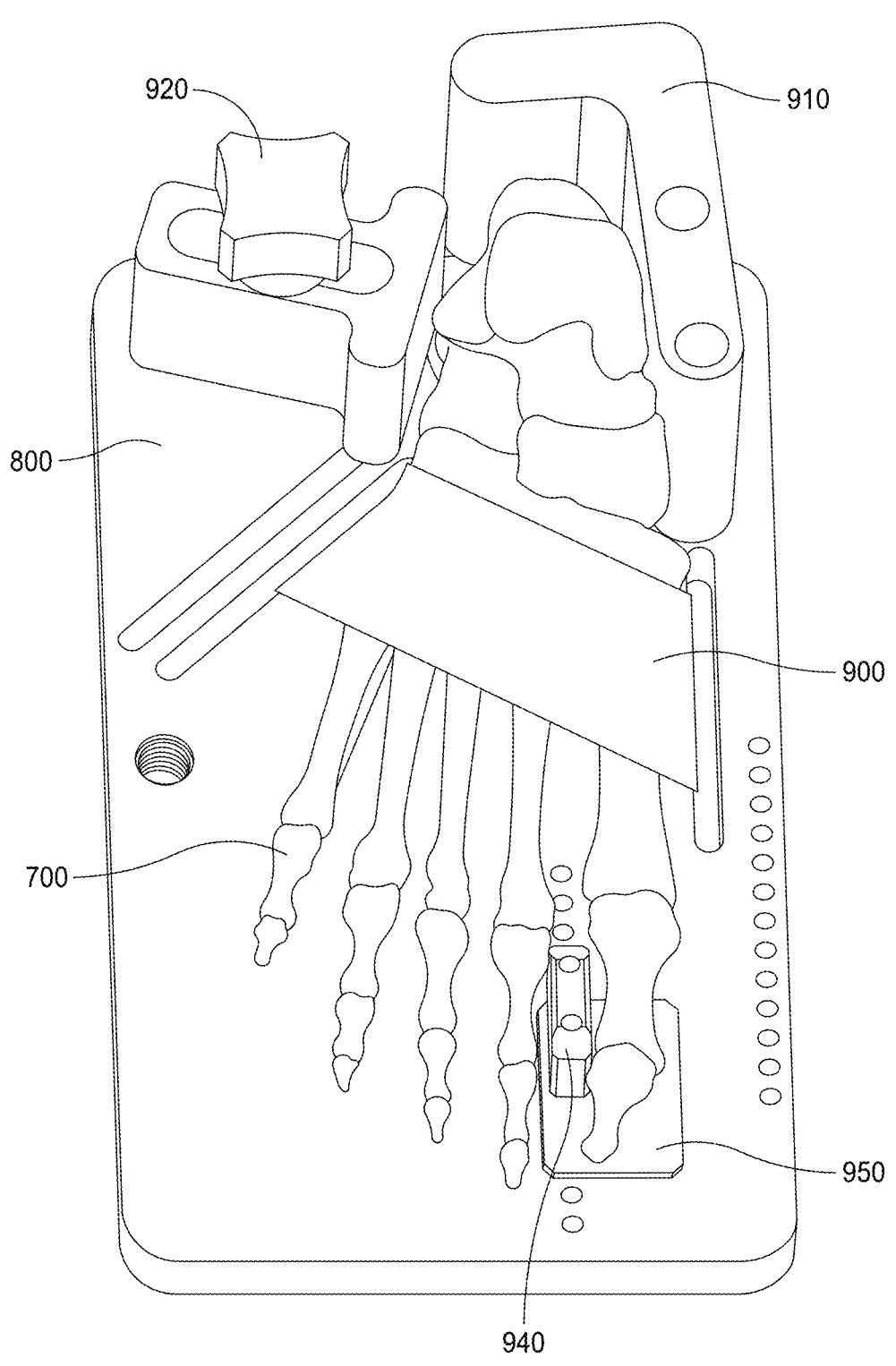
Figure 16:
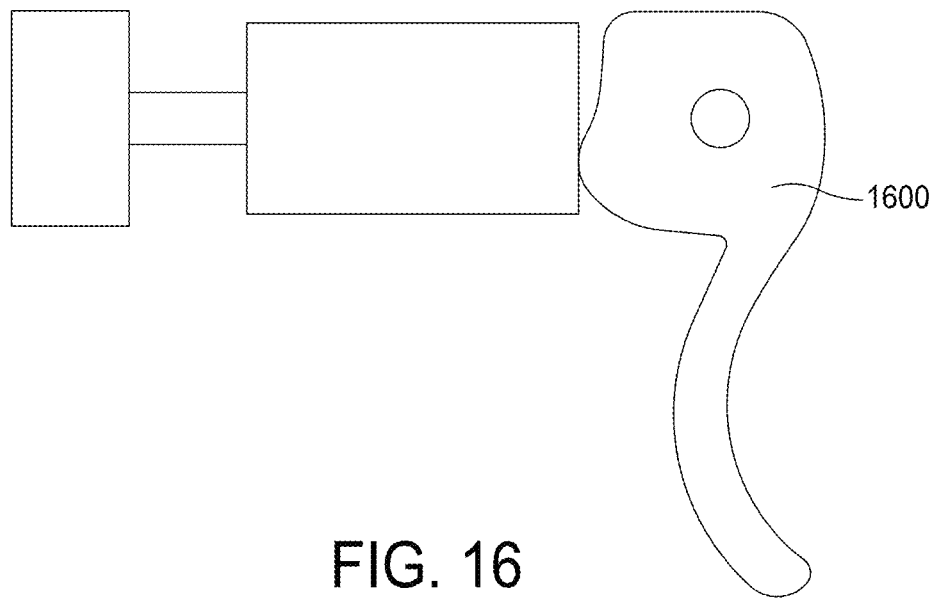
FIG. 16 is a side view of a cam mechanism.

The location of the pusher 930 and the support 940 along respective slots can be locked in place with, for example, a screw mechanism or a lever and cam mechanism, like that shown in FIG. 16. The hallux-valgus pusher 930 and a lateral phalanx support 940 can be located within the pegboard holes 840 to fit the foot 700. The hallux-valgus pusher 930 and the phalanx support 940 features can be placed as proximally or as distally as needed to accommodate the foot size. The hallux-valgus pusher 930 can include an adjustment mechanism such as including a body with a threaded hole and a knob to a lead screw and a dowel or dowels, to ensure that turning the knob strictly results in linear translation, through the threaded hole to a push plate to provide a force against the MTP joint and leverage the phalanx against the phalanx support 940 to straighten or align the metatarsal and the phalanx at the surgeon's discretion. Additionally, FIG. 13 shows that a shim 950 can be optionally placed under the phalanx and held in place via the phalanx support 940 to assist in bone alignment. The shim 950 can be one of a set of shims having different thicknesses to provide varying amounts of vertical alignment of the phalanx.

Once the plate 800 is secured to the patient's foot and the foot is aligned as desired, the surgeon can apply a force to the plate 800 as a whole to simulate weight bearing on the foot during whatever procedure is being performed.

Figure 14:
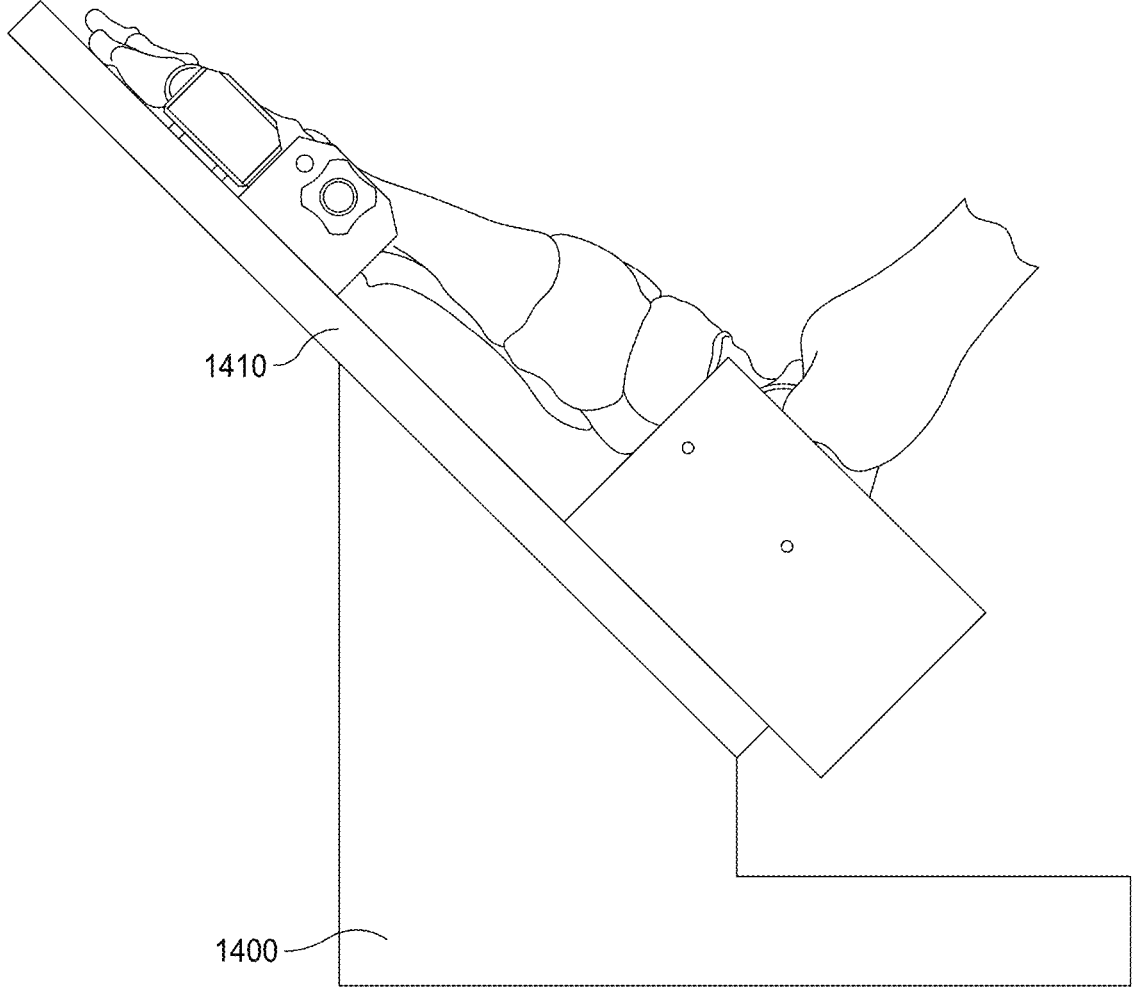
FIG. 14 and FIG. 15 show a weight-bearing simulator according to another embodiment of the present disclosure.
Figure 15:
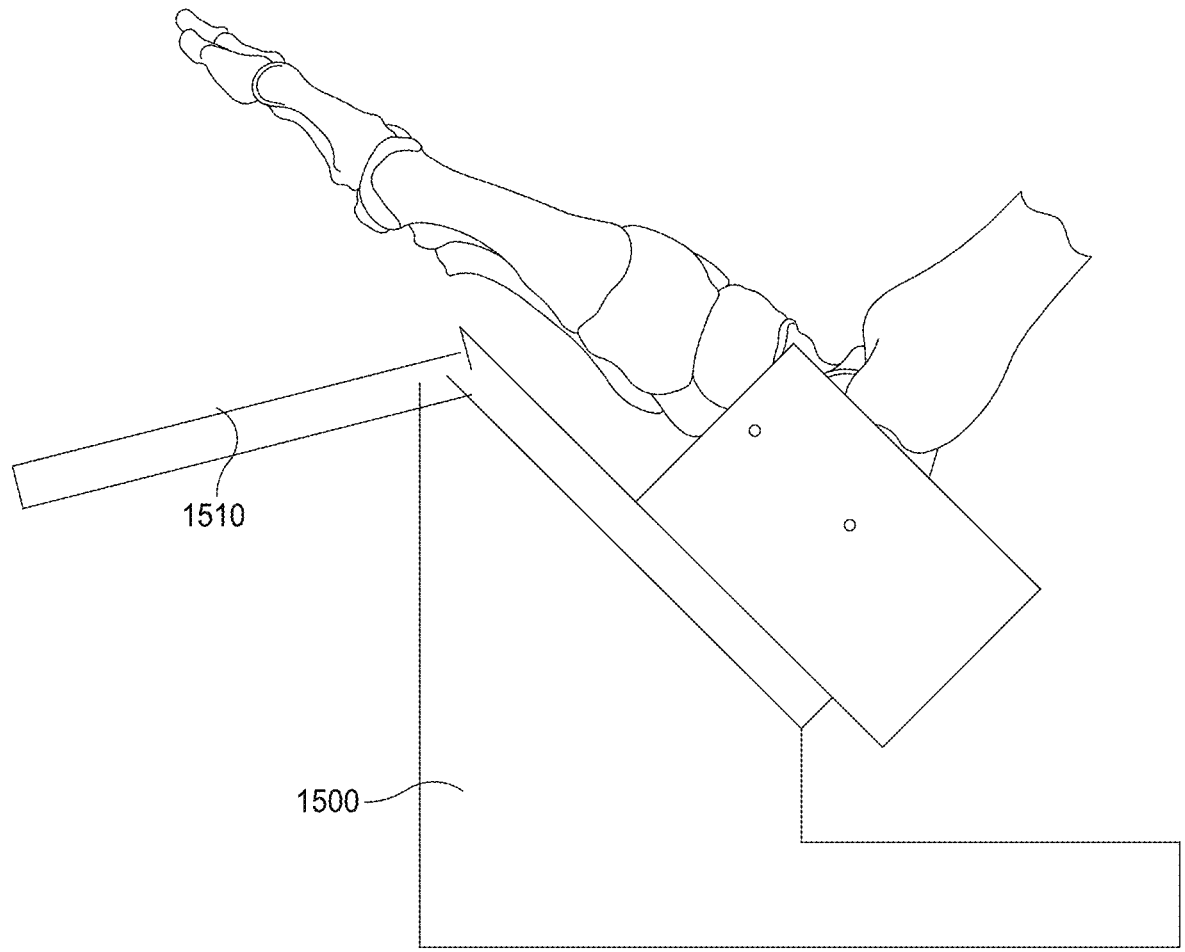

FIGS. 14 and 15 show a weight-bearing simulator according to another embodiment of the present disclosure. This embodiment permits the patient's foot to be held in a position above the operating room table or other supporting surface to provide weight bearing. FIG. 14 is a side view of a system to provide weight bearing simulation that includes a support 1400 and a plate 1410. The plate 1410 can be like any of those previously described. The plate 1410 can be defined as integrated with the support 1400 or be a separate structure that can be attached to or rest on the support 1400. The support 1400 can include a flat bottom surface and an angled surface that supports the plate 1410 such that the plate 1410 is angled with respect to the bottom surface.

FIG. 15 is a side view of an aspect to provide weight bearing simulation that includes a support 1500 for a plate 1510 similar to that shown in FIG. 14. However, in this configuration the plate 1510 can be hinged. As such, the plate 1510 can be made to drop away a distal portion of the plate 1510 to facilitate 3600 of access to the forefoot during surgery. Thus, the plate 1510 can include a mechanism to lock and release the hinged portion of the plate 1510.

Figure 18:
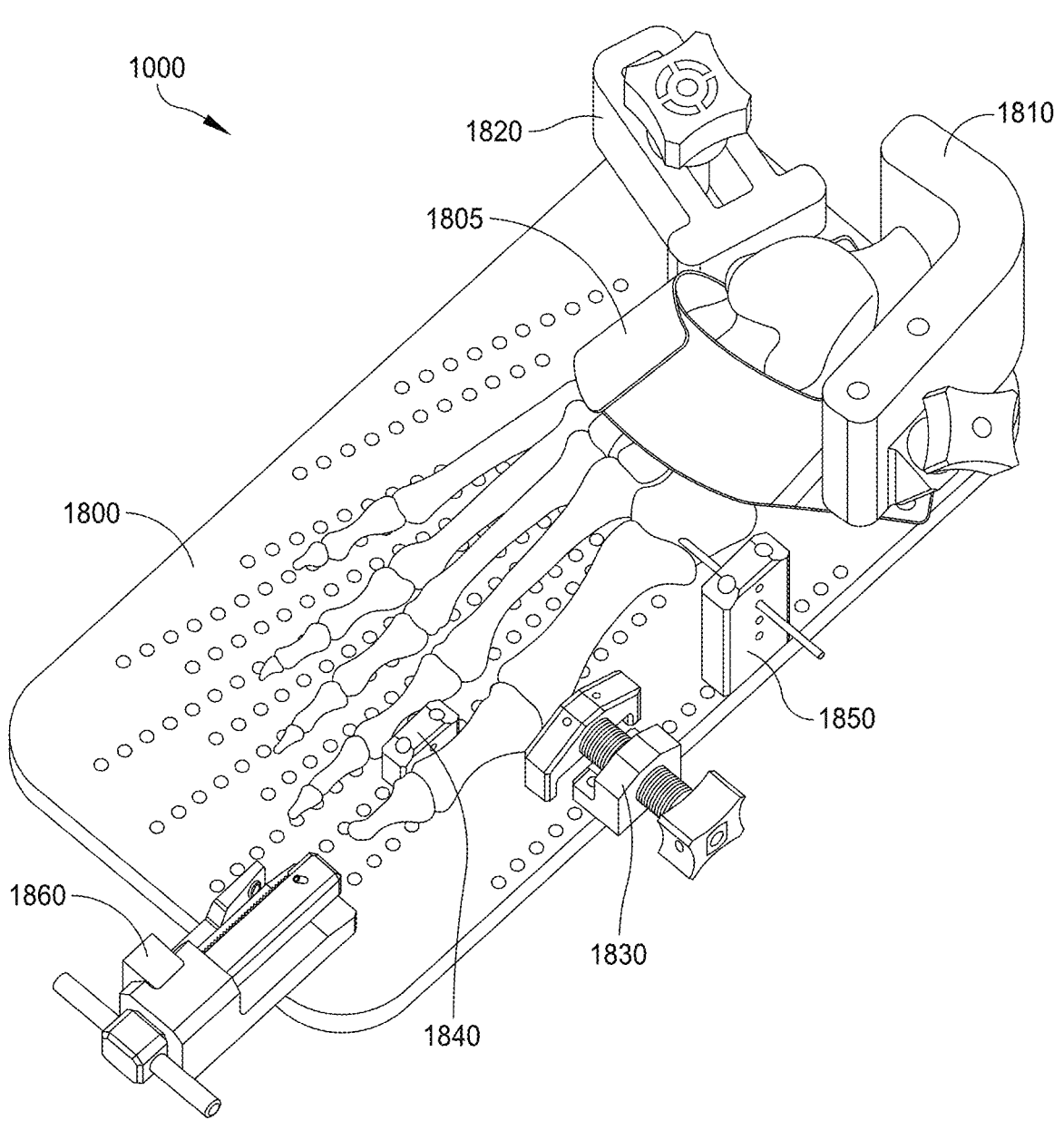
FIG. 18 shows a system to provide weight bearing simulation and foot surgery according to another embodiment.
Figure 19:
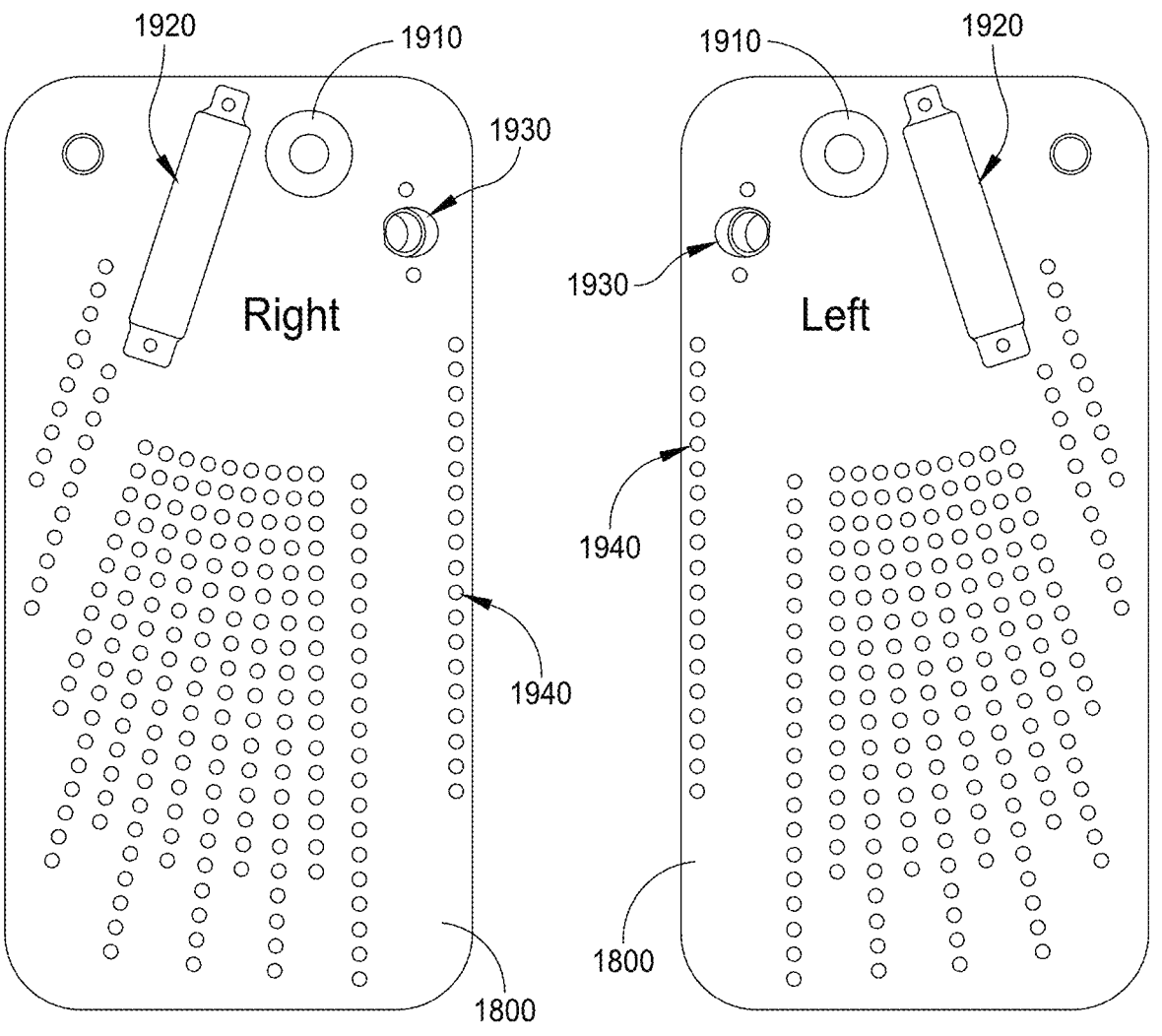
FIG. 19A and FIG. 19B are views of two sides of a plate.

FIGS. 18-27 are used to describe another embodiment of the present disclosure. This embodiment has some similar features like that described with respect to FIGS. 8-13. The system 1000 of this embodiment also provides features to fixate feet of variable lengths to one flat, sturdy, radiolucent plate 1800 for simulated weight bearing. As shown in FIG. 18, the system 1000 can include the plate 1800, a strap 1805, a posterior-medial heel block 1810, a lateral heel block 1820, a hallux-valgus pusher 1830, a lateral phalanx support 1840, a stabilizer 1850, and a toe distractor 1860. The features of the strap 1805, the posterior-medial heel block 1810, the lateral heel block 1820, the hallux-valgus pusher 1830, and the lateral phalanx support 1840 are similar to those previously described, a description of which is omitted for brevity.

FIG. 19A depicts one side of the plate 1800 used for a right foot and FIG. 19B depicts the opposite side of the plate 1800 used for a left foot. The plate 1800 can be substantially planar. Although shown as having a rectangular shape with rounded corners, the plate 1800 can be defined to have any suitable shape. The features provided on the plate 1800 can include a heel locator 1910, a slot 1920, a plurality of fixture holes 1930, and a plurality of peg board holes 1940.

The heel locator 1910 can be a recess, depression, hole, or marked indicator in the plate 1800 in which a patient's heel can be located. The slot 1920 can be used to route the adjustable strap 1805 through the plate 1800 and across a mid-foot to secure the plate 1800 to the patient's foot, as described with respect to FIG. 9. The plurality of fixture holes 1930 can be used to mount blocks or fixtures to orient and secure the patient's foot, as described with respect to FIGS. 10 and 11. The plurality of pegboard holes 1940 can be used to mount blocks or adjustment fixtures to orient and secure bones of the patient's foot, as described with respect to FIGS. 12 and 13. Optionally, the pegboard holes 1940 can be replaced with a slot, as discussed with respect to FIG. 17. The plurality of pegboard holes 1940 provide various mounting options to secure the system features depending on the patient's anatomy and surgeon's preferences.

Figure 20:
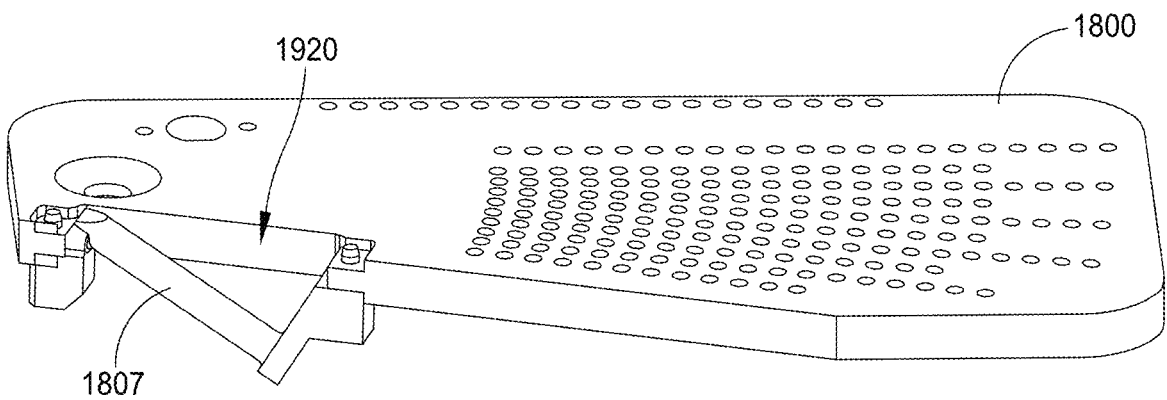
FIG. 20 is a section view of the plate.
Figure 21:
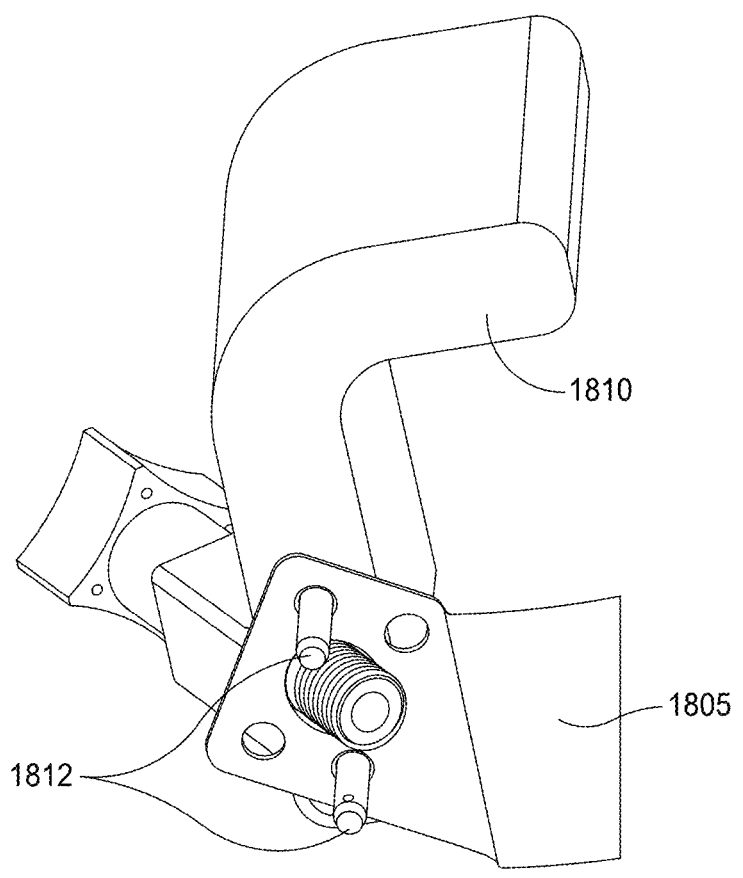
FIG. 21 shows a strap attached to a heel block.
Figure 22:
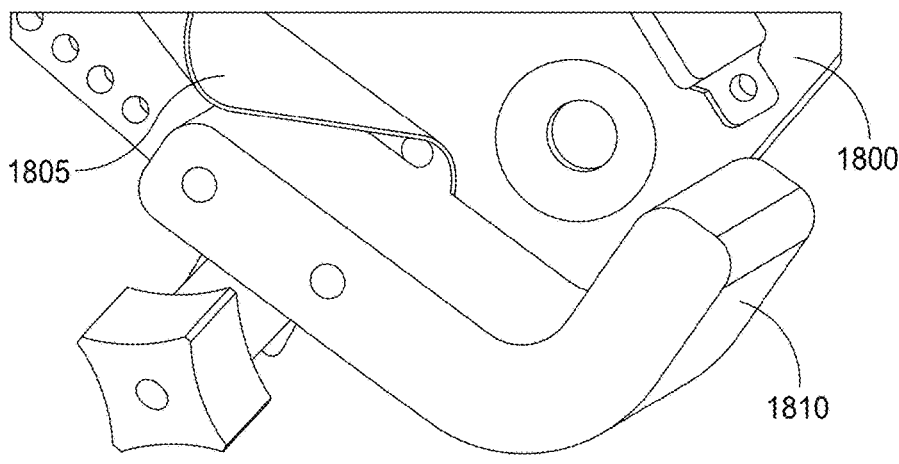
FIG. 22 shows the heel block attached to the plate.

In use, a plate 1800 can be selected and oriented to mate with the patient's foot. FIG. 20 is a section view of the plate 1800 showing that an angled webbing guide 1807 can be mounted under the slot 1920 from the bottom. One end of the strap 1805 can be threaded onto right or left heel support pegs 1812 of the posterior-medial heel block 1810, as shown in FIG. 21 and then the posterior-medial heel block 1810 can be assembled to the plate 1800 by threading to lock it firmly, as shown in FIG. 22.

Figure 23:
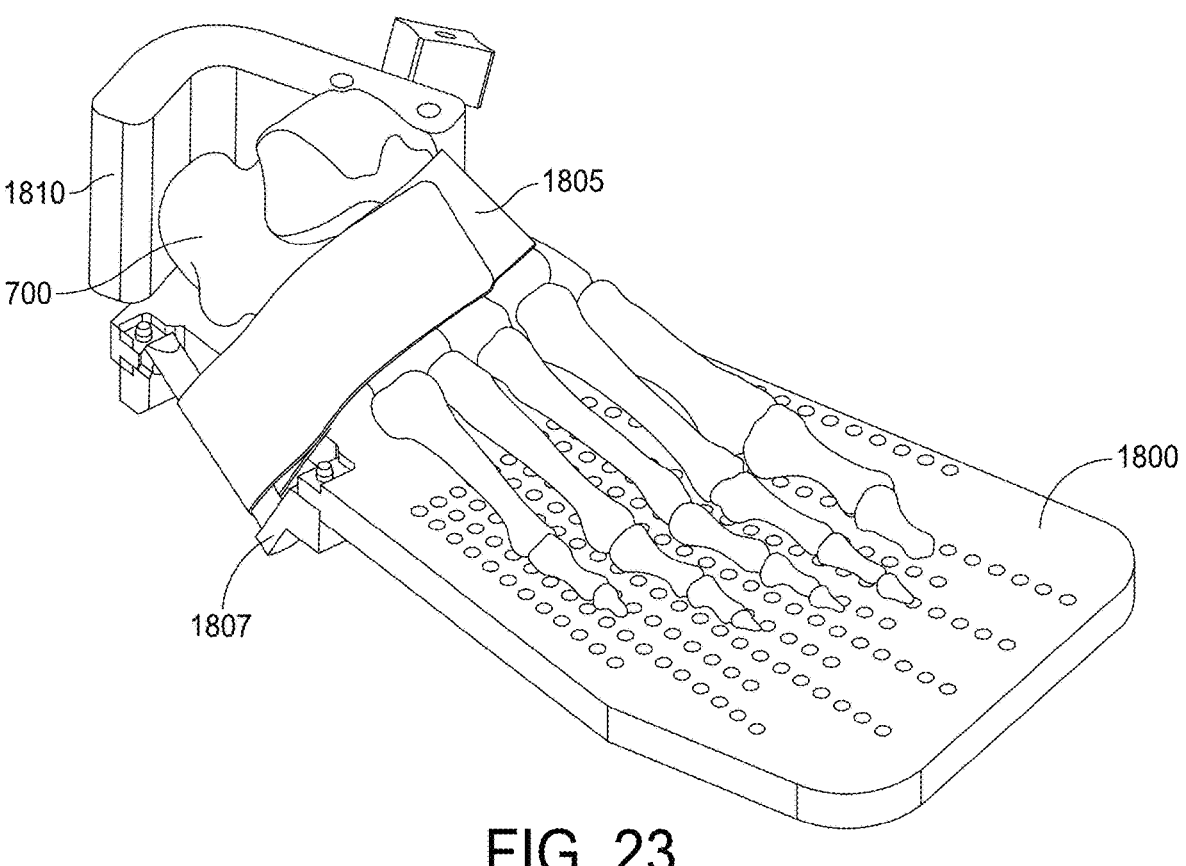
FIG. 23 shows a patient's foot secured to the plate 1800.
Figure 24:
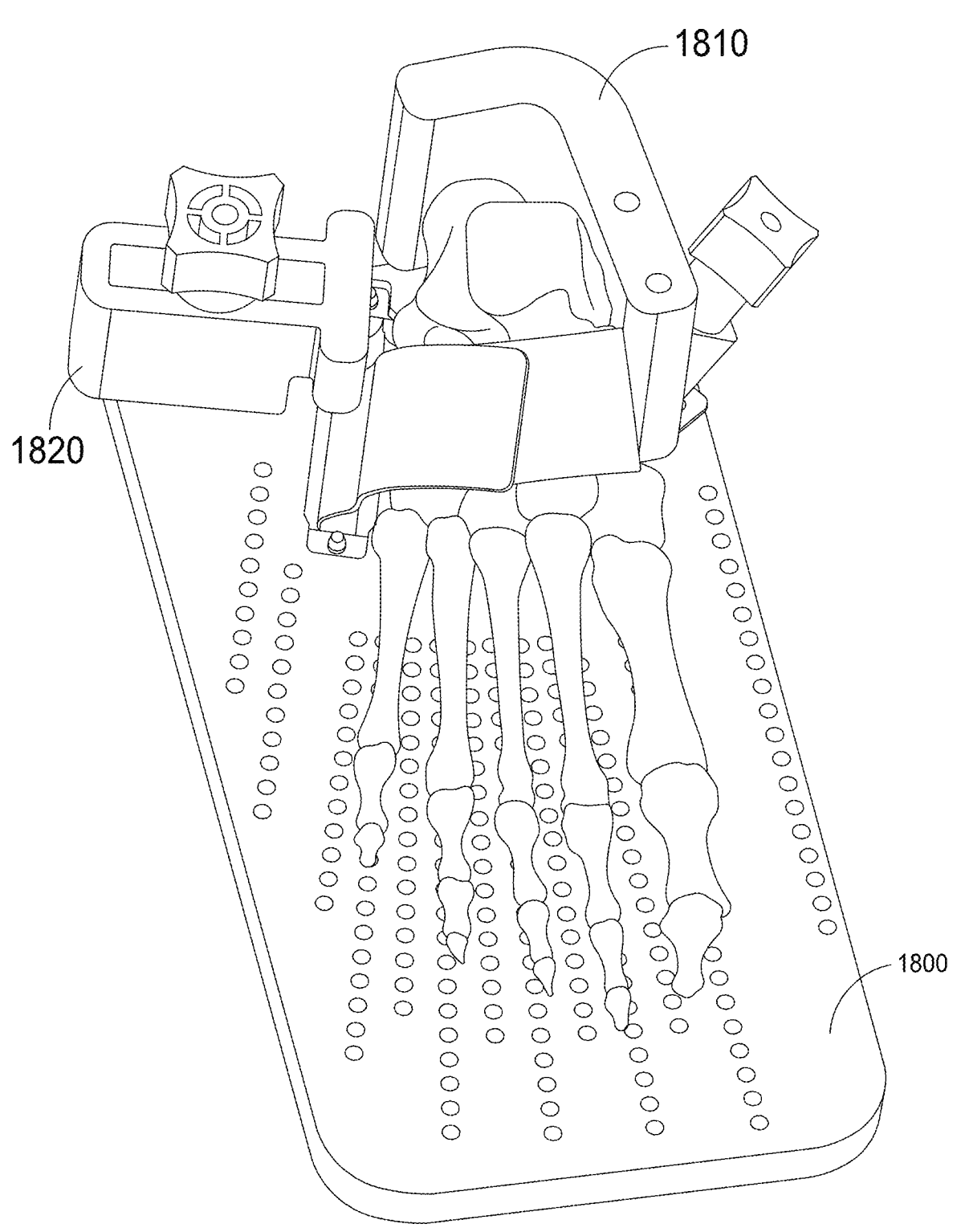
FIG. 24 shows a lateral heel support attached to the plate and tightened to the calcaneus of the patient's foot.

FIG. 23 shows that the patient's foot 700 can be placed on the plate 1800 and the strap 1805 can be threaded around the angled webbing guide 1805 and locked onto itself to secure the plate 1800 to the foot 700. Next, the lateral heel support 1820 can be attached to the plate 1800 and tightened to the calcaneus of the patient's foot 700, as shown in FIG. 24. The stabilizer 1850 shown in FIG. 18 can be used to help secure the patient's foot 700 to the plate 1800. The stabilizer 1850 can be mounted to a suitable position on the plate 1800 using dowels with spring plungers into pegboard holes 1940. A k wire can be place through the stabilizer 1850 and into a bone of the patient's foot 700 to limit movement of the foot 700 with respect to the plate 1800.

Figure 25:
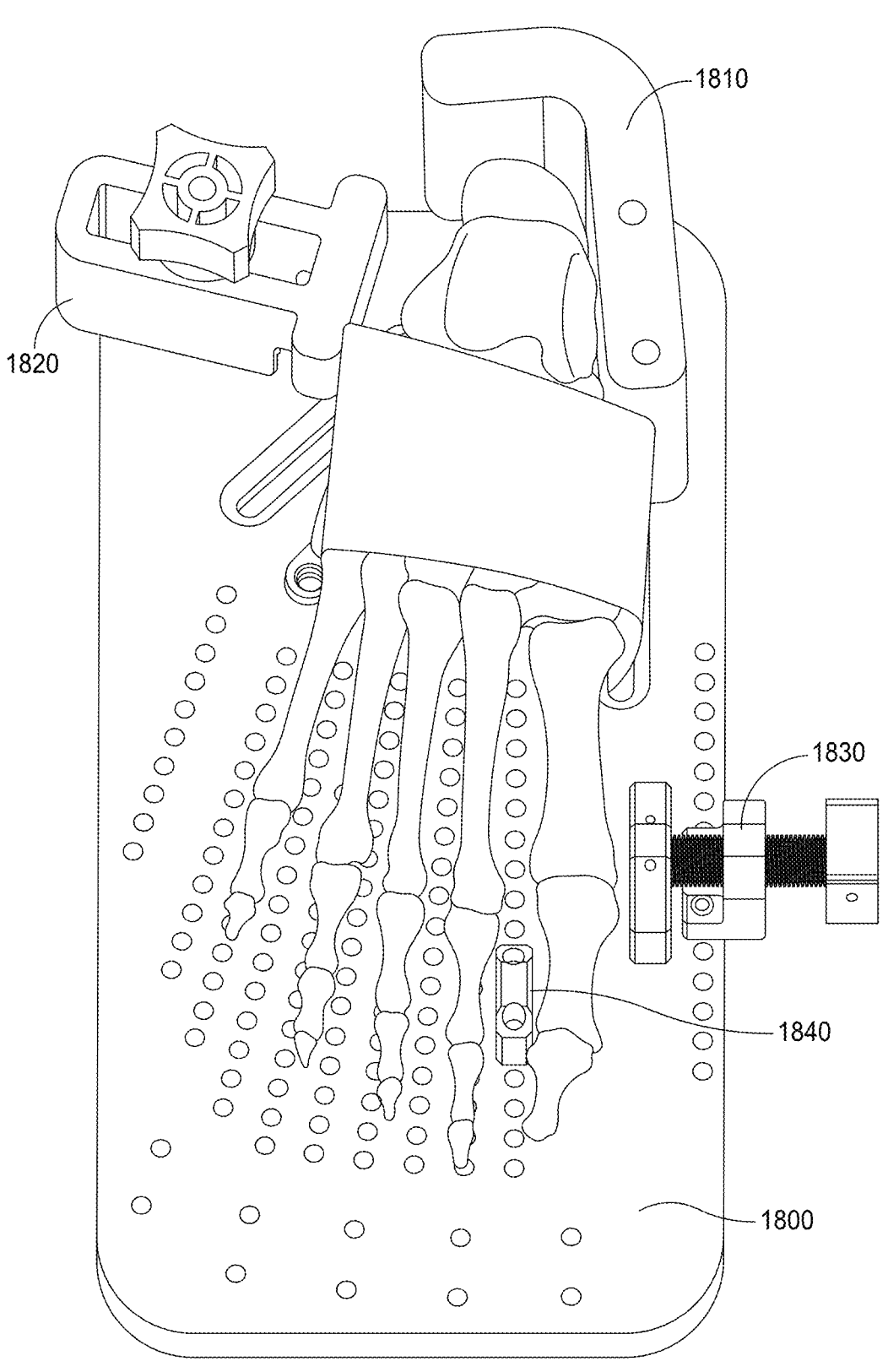
FIG. 25 shows a pusher attached to the plate.

The hallux-valgus pusher 1830 and the lateral phalanx support 1840 can be secured to the plate 1800 and the knob on hallux-valgus pusher 1830 can be turned for MTP joint alignment and correction, as shown in FIG. 25.

Figure 26:
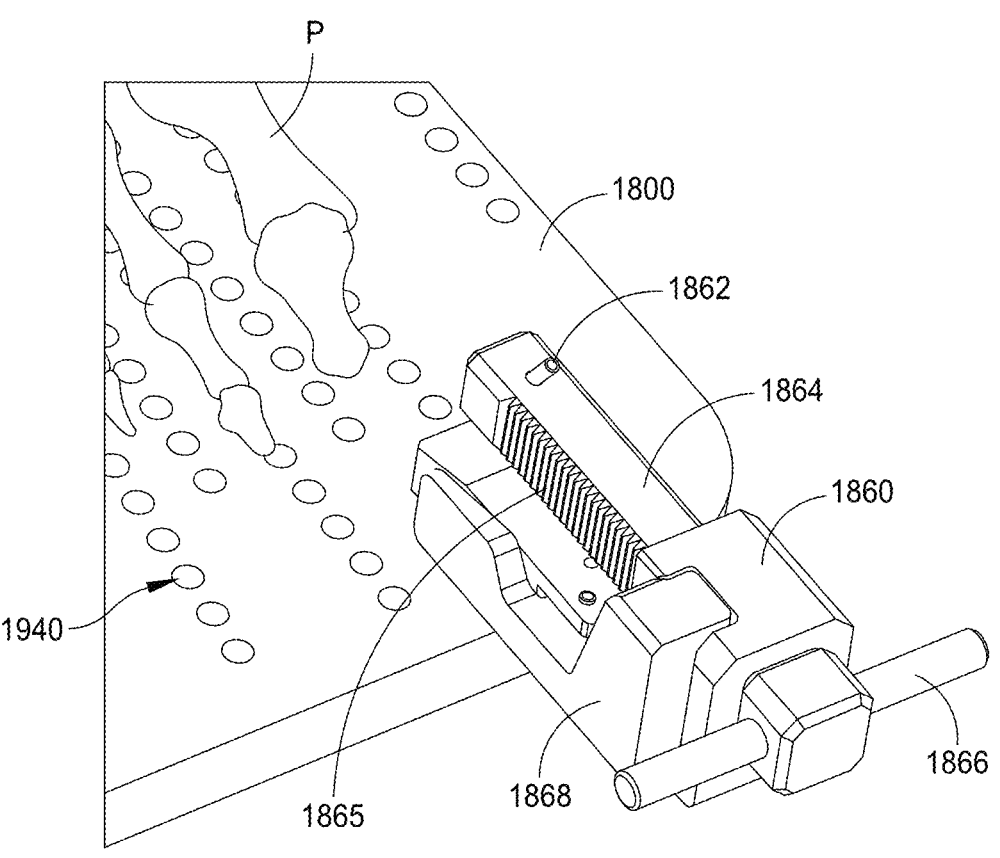
FIG. 26 and FIG. 27 are views of a toe distractor.
Figure 27:
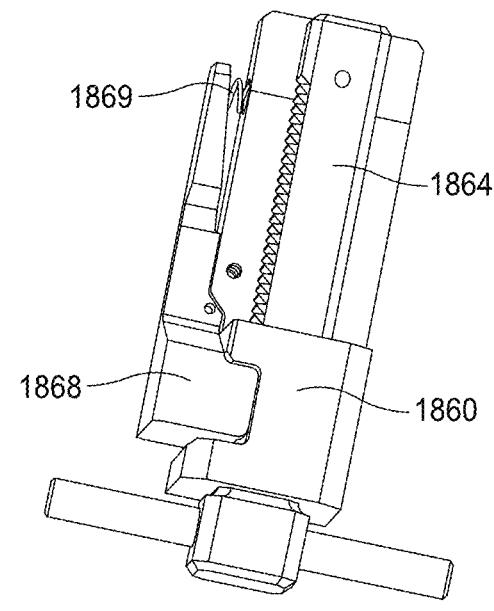

The system 1000 can include the toe distractor 1860 shown in the close up view of FIG. 26. The toe distractor 1860 can be used to provide a force in a longitudinal direction of the toe bones, for example, to separate the phalanx P from the metatarsal at the MTP joint. The toe distractor 1860 can be mounted to the plate 1800 using dowels with spring plungers into pegboard holes 1940. The patient's phalanx P can be attached to the toe distractor 1860 using a to grabber such as a sock, sleeve, or other suitable construct (not shown) that applies pressure to hold on to the bone and hook or wrap around a pin 1862 that is attached to and protruding from a ratchet shaft 1864. The MTP joint can be distracted by pulling the ratchet shaft 1864 and attached phalanx P away from the MTP joint via handle 1866. This action draws teeth 1865 of the ratchet shaft 1864 through a lock 1868 such that the teeth 1865 are held by the lock 1868 and prevents the ratchet shaft 1864 and attached phalanx P from moving toward the MTP joint. After the MTP joint has been treated or repaired, the phalanx P can be released to return back toward the MTP joint by releasing the lock 1868. Pressing on an end of the lock 1868 can compress a spring 1869, shown in FIG. 27, and lever the lock 1868 away from the teeth 1865 and allow the ratchet shaft 1864 to move toward the patient's foot.

It should be understood that the foregoing description is only illustrative of the present invention. Various alternatives and modifications can be devised by those skilled in the art without departing from the present invention. Accordingly, the present invention is intended to embrace all such alternatives, modifications, and variances that fall within the scope of the appended claims.

What is claimed is:

1. A system to provide weight bearing simulation, the system comprising:
   a radiolucent, substantially planar plate having a superior surface and an inferior surface, the plate including a heel locator and a midfoot region and defining a through-slot located between the heel locator and the midfoot region;
   an angled webbing guide mounted to the inferior surface of the plate under the through-slot;
   a strap routed from the superior surface through the through-slot to the inferior surface and around the angled webbing guide and back to the superior surface, the strap configured to hold the plate to a patient's foot across the midfoot region;

a posterior-medial heel block attachable to the plate adjacent the heel locator and including heel support pegs to which an end of the strap is attachable; and a lateral heel block attachable to the plate opposite the posterior-medial heel block and including a body and a knob configured to tighten the lateral heel block against a calcaneus of the patient's foot to clamp the heel of the patient's foot between the posterior-medial heel block and the lateral heel block.

2. The system of claim 1, wherein the plate includes a plurality of holes to mount the lateral heel block.

3. The system of claim 2, wherein the lateral heel block is adjustable to accommodate various size feet.

4. The system of claim 1, wherein a first side of the plate is configured to be secured to a right foot and a second side of the plate is configured to be secured to a left foot.

5. The system of claim 1, wherein the lateral heel block includes a pusher configured to adjust a position of a bone of the foot.

6. The system of claim 1, wherein the lateral heel block includes a distractor configured to apply force to separate bones of the foot.

7. The system according to claim 1, wherein the plate further includes a plurality of holes arranged to receive mounting features of the posterior-medial heel block and the lateral heel block.

8. The system of claim 7, wherein the plate further includes a plurality of pegboard holes arranged to receive a hallux-valgus pusher and a lateral phalanx support for aligning metatarsophalangeal bones while the plate is secured to the foot.

9. The system of claim 8, wherein the system is configured to simulate weight bearing by enabling application of force to the plate as a whole while the foot is secured to the radiolucent, substantially planar plate by the strap and the medial and lateral heel blocks.

10. A system to provide weight bearing simulation, the system comprising:

a radiolucent, substantially planar plate having a superior surface, an inferior surface, a heel locator, and a through-slot located between the heel locator and a midfoot region of the plate, an angled webbing guide mounted to the inferior surface of the plate under the through-slot, a strap routed from the superior surface through the through-slot to the inferior surface and around the angled webbing guide and back to the superior surface, the strap configured to hold the plate to a patient's foot across the midfoot region, a posterior-medial heel block attachable to the plate adjacent the heel locator and including heel support pegs to which an end of the strap is attachable, and a lateral heel block attachable to the plate opposite the posterior-medial heel block and including a body and a knob configured to tighten the lateral heel block against a calcaneus of the patient's foot to clamp the heel of the patient's foot between the posterior-medial heel block and the lateral heel block;

a clamp configured to secure the plate by compressing the plate between a base and an opposing arm with a screw driven through the arm toward the base to generate clamping force; and an adjuster attached to the arm of the clamp and including a body, a lead screw oriented perpendicular to a weight-bearing plane defined by the plate to provide linear adjustment in a superior-inferior direction, and a guide interface coupled to the body, the guide interface being configured to mount a surgical guide and to be tightened or loosened relative to the body with a second screw; wherein the surgical guide is mountable to the guide interface via posts on the guide interface receivable in corresponding holes of the surgical guide and a locking tab operable to retain the surgical guide on the posts, wherein the clamp and adjuster are configured to position the surgical guide relative to the patient's foot in contact with the plate while the plate is secured by the clamp to simulate weight bearing during foot surgery.

11. The system of claim 10, wherein the adjuster includes a lead screw and dowel mechanism.

12. The system of claim 10, wherein the adjuster includes a body, a lead screw, and a guide interface.

13. The system of claim 12, wherein the guide interface is configured to mount a surgical guide.

14. A method of performing foot surgery comprising:

providing a radiolucent, substantially planar plate having a superior surface and an inferior surface, the plate including a heel locator and a midfoot region and defining a through-slot located between the heel locator and the midfoot region;

an angled webbing guide mounted to the inferior surface of the plate under the through-slot;

a strap routed from the superior surface through the through-slot to the inferior surface and around the angled webbing guide and back to the superior surface, the strap configured to hold the plate to a patient's foot across the midfoot region;

a posterior-medial heel block attachable to the plate adjacent the heel locator and including heel support pegs to which an end of the strap is attachable; and a lateral heel block attachable to the plate opposite the posterior-medial heel block and including a body and a knob configured to tighten the lateral heel block against a calcaneus of the patient's foot to clamp the heel of the patient's foot between the posterior-medial heel block and the lateral heel block; and securing the patient's foot to the radiolucent, substantially planar plate.

15. The method of claim 14, wherein securing the foot to the plate includes locking the heel of the patient's foot into place on the radiolucent, substantially planar plate.

16. The method of claim 14, wherein securing the foot to the plate includes mounting a stabilizer to the plate and inserting a k wire through the stabilizer and into the foot.

17. The method of claim 14, further comprising simulating weight bearing by applying a force to the foot via the plate.

18. The method of claim 14, further comprising: attaching a guide to the plate; and adjusting alignment of a first bone and a second bone using the guide.

19. The method of claim 18, further comprising distracting the first bone and the second bone using the guide.

* * * * *